US010045738B2

(12) United States Patent
Bracke et al.

(10) Patent No.: US 10,045,738 B2
(45) Date of Patent: Aug. 14, 2018

(54) TISSUE RESISTANCE MEASUREMENT

(71) Applicant: MEDTRONIC BAKKEN RESEARCH CENTER B.V., Maastricht (NL)

(72) Inventors: Wouter Hubert Martha Adelaïde Bracke, Heverlee (BE); Jeroen Jacob Arnold Tol, Eindhoven (NL); Egbertus Johannes Maria Bakker, Wijk en aalburg (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 314 days.

(21) Appl. No.: 14/952,675

(22) Filed: Nov. 25, 2015

(65) Prior Publication Data

US 2016/0143591 A1    May 26, 2016

Related U.S. Application Data

(60) Provisional application No. 62/084,252, filed on Nov. 25, 2014.

(51) Int. Cl.
| A61B 5/05 | (2006.01) |
| A61B 5/00 | (2006.01) |
| A61B 5/053 | (2006.01) |
| A61B 5/04 | (2006.01) |
| A61N 1/04 | (2006.01) |
| A61N 1/36 | (2006.01) |
| A61B 5/0478 | (2006.01) |
| A61N 1/05 | (2006.01) |

(52) U.S. Cl.
CPC ........ *A61B 5/7203* (2013.01); *A61B 5/04001* (2013.01); *A61B 5/0538* (2013.01); *A61N 1/0476* (2013.01); *A61N 1/0488* (2013.01); *A61N 1/0529* (2013.01); *A61N 1/36125* (2013.01); *A61B 5/0478* (2013.01); *A61N 1/0534* (2013.01)

(58) Field of Classification Search
CPC . A61B 5/7203; A61B 5/04001; A61B 5/0538; A61N 1/0476; A61N 1/0488; A61N 1/0529; A61N 1/36125
USPC ........................................................ 600/547
See application file for complete search history.

(56) References Cited

U.S. PATENT DOCUMENTS

| 5,063,937 A * | 11/1991 | Ezenwa ............... A61B 5/0535 600/536 |
| 7,391,257 B1 | 6/2008 | Denison et al. |
| 7,622,988 B2 | 11/2009 | Denison et al. |
| 7,941,202 B2 | 5/2011 | Hetke et al. |

(Continued)

FOREIGN PATENT DOCUMENTS

| WO | 2010055453 A1 | 5/2010 |
| WO | 2011107917 A1 | 9/2011 |

*Primary Examiner* — Daniel Cerioni
(74) *Attorney, Agent, or Firm* — Shumaker & Sieffert, P.A.

(57) ABSTRACT

The disclosure describes tissue resistance measurement techniques. To avoid errors caused by bandwidth limitations of the amplifier that amplifies a signal used to determine the tissue resistance, the disclosure describes determining values at different frequencies, where the values include respective error values. The respective error values are proportional to the respective frequencies, and based on this relationship the error value can be removed from the tissue resistance measurement.

20 Claims, 13 Drawing Sheets

(56) References Cited

U.S. PATENT DOCUMENTS

| | | | |
|---|---|---|---|
| 2003/0105411 A1* | 6/2003 | Smallwood | A61B 5/053 600/547 |
| 2009/0030336 A1* | 1/2009 | Woo | A61B 5/0537 600/547 |
| 2009/0079607 A1 | 3/2009 | Denison et al. | |
| 2010/0030086 A1 | 2/2010 | Zielinski et al. | |
| 2010/0033240 A1 | 2/2010 | Denison et al. | |
| 2010/0327887 A1 | 12/2010 | Denison et al. | |
| 2011/0068861 A1 | 3/2011 | Denison | |
| 2011/0080181 A1* | 4/2011 | Sato | A61B 5/0537 324/692 |
| 2011/0098765 A1* | 4/2011 | Patel | A61N 1/08 607/8 |
| 2013/0035606 A1* | 2/2013 | Wichner | A61B 5/7203 600/546 |
| 2013/0169361 A1 | 7/2013 | Killat | |
| 2013/0268019 A1* | 10/2013 | Gupta | A61N 1/36067 607/45 |

* cited by examiner

TISSUE RESISTANCE MEASUREMENT

This application claims the benefit of U.S. Provisional Application No. 62/084,252, filed Nov. 25, 2014, the entire content of which is hereby incorporated by reference in its entirety.

TECHNICAL FIELD

The disclosure relates to tissue resistance measurement.

BACKGROUND

Implantable medical devices, such as electrical stimulators or therapeutic agent delivery devices, have been proposed for use in different therapeutic applications, such as deep brain stimulation (DBS), spinal cord stimulation (SCS), pelvic stimulation, gastric stimulation, peripheral nerve stimulation, functional electrical stimulation. In some therapy systems, an implantable electrical stimulator delivers electrical therapy to a target tissue site within a patient with the aid of one or more electrodes, which may be deployed by medical leads, on a housing of the electrical stimulator, or both.

During a programming session, which may occur during implant of the medical device, during a trial session, or during an in-clinic or remote follow-up session after the medical device is implanted in a patient, a clinician may generate one or more therapy programs (also referred to as therapy parameter sets) that provide efficacious therapy to the patient, where each therapy program may define values for a set of therapy parameters. A medical device may deliver therapy to the patient according to one or more stored therapy programs. In the case of electrical stimulation, the therapy parameters may define characteristics of the electrical stimulation waveform to be delivered.

SUMMARY

The disclosure describes example techniques for resistance measurement. For instance, the techniques may reduce, or otherwise remove, an error value in a resistance measurement, where the error is caused due to circuit bandwidth limitations. For example, for tissue resistance measurement, a medical device includes an amplifier that receives an input signal that includes a real-part and an imaginary-part, and outputs a signal that includes a real-part and an imaginary-part. The amplitude of the real-part of the input signal is a function of the tissue resistance, and the imaginary-part of the input signal is a function of reactance in a signal path to the tissue. The input and output signals may be modulated signals with a certain frequency. The medical device determines the tissue resistance based on the real-part of the output signal (e.g., after further processing of the output signal to remove the imaginary-part).

In this disclosure, the terms "real-part" and "imaginary-part" are used to differentiate between signals generated from resistive and reactive components. The real-part is from resistance, and the imaginary-part is generated form reactive components like capacitors and inductors. The term "imaginary" should not be interpreted to mean that this so-called imaginary-part does not exist, but rather as a way to differentiate the signal types.

Ideally, the real-part of the output signal is a rectangular wave. However, due to bandwidth limitations of the amplifier, the real-part of the output signal is not a rectangular wave, resulting in errors in the tissue resistance determination. In the techniques described in this disclosure, the medical device may generate the output signal at different frequencies (e.g., a plurality of signals outputted by the amplifier). In each of the output signals, there is a portion related to the actual tissue resistance, and a portion related to the respective error values. The actual tissue resistance is not a function of the signal frequency, but the respective error values may be a function of the signal frequency (e.g., in instances where the further processing of the output of the amplifier is performed at the same frequency as the frequency of the input or output signal). Because the error value is a function of the signal frequency and the actual tissue resistance is not, the medical device may be able to remove the error value based on the different frequencies of the different output signals.

In one example, the disclosure describes a method for tissue resistance measurement, the method comprising generating, at an electrode, a first electrical signal of a first type through outputting, via the electrode, a first electrical signal of a second type at a first frequency, processing the first electrical signal of the first type at the first frequency to generate a first output signal, generating, at the electrode, a second electrical signal of the first type through outputting, via the electrode, a second electrical signal of the second type at a second, different frequency, processing the second electrical signal of the first type at the second frequency to generate a second output signal, and determining a tissue resistance at the electrode based on the first output signal, the second output signal, and a ratio between the first frequency and the second frequency.

In another example, the disclosure describes a system for tissue resistance measurement, the system comprising at least one electrical signal source configured to generate, at an electrode, a first electrical signal of a first type through outputting, via the electrode, a first electrical signal of a second type at a first frequency, and generate, at the electrode, a second electrical signal of the first type through outputting, via the electrode, a second electrical signal of the second type at a second, different frequency. The system also includes resistance measurement circuitry configured to process the first electrical signal of the first type at the first frequency to generate a first output signal, and process the second electrical signal of the first type at the second frequency to generate a second output signal. The system also includes a processor configured to determine a tissue resistance at the electrode based on the first output signal, the second output signal, and a ratio between the first frequency and the second frequency.

In another example, the disclosure describes a system for tissue resistance measurement, the system comprising means for generating, at an electrode, a first electrical signal of a first type through outputting, via the electrode, a first electrical signal of a second type at a first frequency, means for processing the first electrical signal of the first type at the first frequency to generate a first output signal, means for generating, at the electrode, a second electrical signal of the first type through outputting, via the electrode, a second electrical signal of the second type at a second, different frequency, means for processing the second electrical signal of the first type at the second frequency to generate a second output signal, and means for determining a tissue resistance at the electrode based on the first output signal, the second output signal, and a ratio between the first frequency and the second frequency.

The details of one or more examples are set forth in the accompanying drawings and the description below. Other

DETAILED DESCRIPTION

Figure 1:
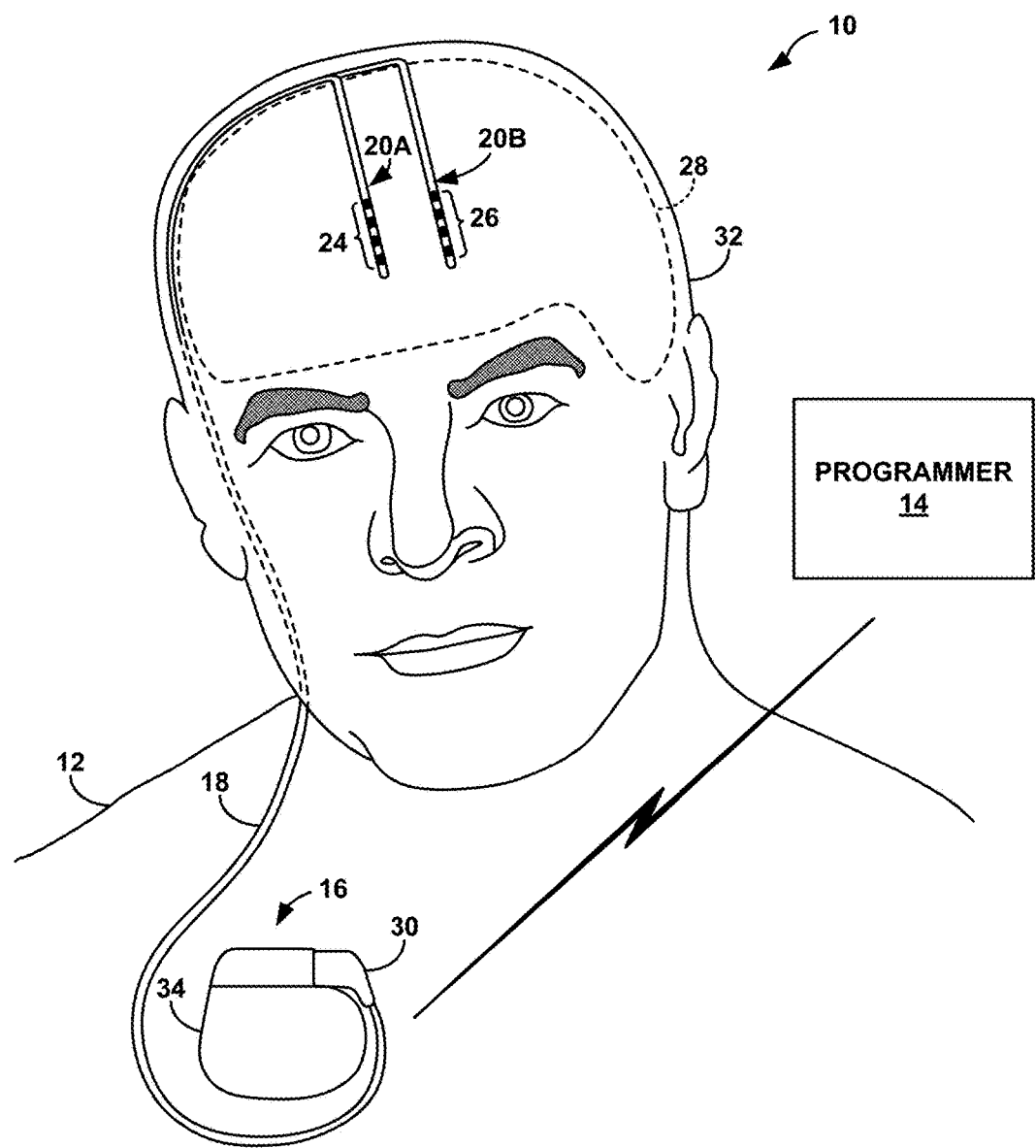
FIG. 1 is a conceptual diagram illustrating an example deep brain stimulation (DBS) system configured to sense a bioelectrical brain signal and deliver electrical stimulation therapy to a tissue site within a brain of a patient.

A medical device, such as an implantable medical device (IMD), may be configured to determine the resistance of tissue such as, e.g., human tissue. By determining the resistance of tissue, the IMD or a clinician can determine therapy parameters (e.g., amplitude) of electrical neurostimulation (e.g., voltage or current) outputted by the IMD to provide proper neurostimulation therapy.

One example way in which to determine the tissue resistance is for the IMD to output a current via electrodes coupled to the tissue, determine a voltage caused by the flow of current through the tissue, and divide the voltage by the current to determine the tissue resistance. Conversely, the IMD may output a voltage via electrodes coupled to the tissue, determine a current caused by the voltage applied to the tissue, and divide the voltage by the current to determine the tissue resistance. For ease of description, the techniques are described with respect to a flow of current.

However, the flow of direct current (DC) current through tissue may not be advisable, and the IMD may instead output a modulated current or modulated voltage (e.g., such as one that forms a rectangular wave with a particular frequency) via electrodes. This modulated current or modulated voltage is referred to as an excitation signal. The excitation signal may be DC free using push-pull voltage and current sources to create a voltage or current that swings around zero volts. However, due to device error or if the duty cycle between the pus-pull voltage and current sources is not exactly 50%, there may be a slight DC voltage or current. To further ensure that DC current does not flow through tissue, the IMD includes a capacitor in the signal path of the electrode to block the DC current.

The inclusion of the capacitor in the signal path of the electrode adds a reactive component in the signal path, which adds reactance. For example, if there was no capacitor in the signal path, then the voltage caused by the flow of current would only be a function of the resistance of the tissue (i.e., $V=I*R_{tissue}$). However, because there is a capacitor in the signal path, the voltage caused by the flow of current is a function of the resistance of the tissue and the reactance of the capacitor (i.e., $V=I*(R_{tissue}+jX_{capacitor})$). In addition to the capacitor in the signal path, there may other sources of capacitance as well such as capacitance from tissue interface, capacitance in the return path with the housing of the medical device, as well as other possible capacitance sources.

In other words, the voltage caused by the flow of the modulated current includes a real-part (e.g., $I*R_{tissue}$) and an imaginary-part (e.g., $I*jX_{capacitor}$, where j is square-root of −1). Again, this so-called imaginary-part refers to the contribution to the signal from the reactive components such as capacitors, and should not be interpreted to mean that the signal does not exist. By removing the imaginary-part of the voltage signal, the IMD may determine the tissue resistance. One example technique to remove the imaginary-part of the voltage signal is to use a chopper circuit and an averager circuit. For instance, an amplifier may receive input voltage signal that includes the real-part and the imaginary-part. The amplifier outputs a voltage signal (e.g., in examples where the amplifier is a voltage amplifier) or a current signal (e.g., in examples where the amplifier is a transconductance amplifier). In either case, the output signal includes a real-part and an imaginary-part.

As described above, the modulated current may be a rectangular wave with a certain frequency. Because the tissue is predominantly resistive, the real-part of the output signal is still a rectangular wave (assuming a very high bandwidth amplifier), but because the capacitor is reactive and the reactance is a function of frequency, the imaginary-part of the output signal is not a rectangular wave, and is instead a triangular wave.

The chopper circuit receives the output signal, and performs chopping at the same frequency as the frequency of the modulated current. The chopping function can be considered as multiplying the signal by one for half a period, and multiplying the signal by negative one for the other half of the period. Because the chopping frequency is the same as the frequency of the rectangular wave, the chopper circuit results in multiplying the real-part of the output signal by one for the portion of the real-part of the output signal that is positive, and multiplying the imaginary-part of the output signal by negative one for the portion of the real-part of the output signal that is negative, thereby converting the negative portion to a positive value. In this example, in addition to the chopping frequency being the same as the frequency of the rectangular wave, the chopping may be phase aligned with the rectangular-wave (e.g., the chopper circuit multiplies the rectangular wave by one for half a period and switches to multiplying the rectangular wave by negative one for half a period and approximately at the time when the rectangular wave switches from a high to a low).

This way, the chopper circuit converts the real-part of the output signal into a constant value (e.g., constant voltage or current, or DC voltage or DC current). Based on the same principles, the chopper circuit converts the imaginary-part of the output signal into a saw-tooth waveform. An averager circuit (e.g., an averaging analog-to-digital converter) averages the output of the chopper circuit. Because the saw-tooth waveform includes as many positive values as negative values, the averaging of the saw-tooth waveform results in approximately zero (or as described above results in a value that can be compensated for based on measurements during manufacturing). However, the averaging of the constant value results in no change (i.e., the average of the constant values is the constant value).

As described above, the constant value is determined from the real-part of the output signal, which is a function of the tissue resistance, and the saw-tooth waveform is determined from the imaginary-part of the output signal which is a function of the reactance of the capacitor. The averager circuit removes the contribution of the saw-tooth waveform from the output of the chopper circuit, leaving only the constant value. A processor (e.g., of the IMD or of an external device) determines the tissue resistance based on the resulting constant value.

While the chopper circuit and averager circuit may be well suited for determining the tissue resistance, there may be certain drawbacks. For instance, as noted above, the amplifier may need to be very high bandwidth amplifier to ensure that the real-part of the output signal is a rectangular wave. A rectangular wave includes very fast rising and falling edges (i.e., very fast slew rates), and the amplifier would need very high bandwidth to be able to output such a rectangular wave with fast slew rates. However, amplifiers with such high bandwidth tend to be expensive and require high amounts of power for operation.

This disclosure provides example ways in which to utilize amplifiers, without needing the amplifiers to operate at extremely high bandwidth, while still providing accurate tissue resistance measurements. For example, if the amplifier does not provide relatively high bandwidth, the real-part of the output signal is not a rectangular wave, but more of a trapezoidal wave. This trapezoidal wave is referred to as an intermediate electrical signal, as it is between the amplifier and the chopper circuit. In this case, the trapezoidal wave is an input to the chopper circuit, and the output of the chopper circuit is not a constant value for the real-part, but instead a signal that for a portion is approximately equal to the constant value that the chopper circuit would have outputted had the input been a rectangular wave, and for the other portion equal to a value that is not the constant value.

The averager circuit receives the output of the chopper circuit and outputs an average value. In the case of a rectangular output signal to the chopper circuit, the average value that the averager circuit outputs is proportional to the tissue resistance. In the case of a trapezoidal output signal to the chopper circuit, the average value that the averager circuit outputs is a first value, which is proportional to the tissue resistance, plus a second value, which is an error value. If the IMD were to determine the tissue resistance based on this output of the averager circuit, the determined tissue resistance would be the actual tissue resistance plus a resistance error value.

In accordance with the techniques described in this disclosure, the IMD is configured to remove the error value from the output of the averager circuit. One example way in which the IMD may remove the error value from the output of the averager circuit is by applying a plurality (e.g., at least two) of input signals to the electrodes at different modulation frequencies. As described in more detail below, the actual tissue resistance is not a function of the modulation frequency, but the error value is. For instance, if the IMD applies an input signal at a first modulation frequency, the output of the averager circuit would be a first value plus a first error value, where the first error value is a function of the first modulation frequency. If the IMD applies an input signal at a second modulation frequency, the output of the averager circuit would be the same first value plus a second error value, where the second error value is a function of the second modulation frequency. The IMD may then remove the error value based on the two outputs of the averager circuit.

As an example, assume that the output of the averager circuit for a first modulation frequency is a first average value equal to A+B, where A is proportional to the actual tissue resistance and B is an error value and a function of the first modulation frequency. Assume that the output of the averager circuit for a second modulation frequency is a second average value equal to A+C, where A is still proportional to the actual tissue resistance and C is an error value and a function of the second modulation frequency. If the second modulation frequency is N times the first modulation frequency, then the second average value can be rewritten as A+N*B (i.e., because C will equal N*B). In this example, the IMD may multiply the first average value by N, resulting in the value of N*A+N*B, and multiply the second average value by −1, resulting in the value of −A−NB. The IMD may add the two resulting values together, for a value of (N−1)*A, and divide the resulting value by (N−1), resulting in the final value of A. As described above, the value of A is proportional to the actual tissue resistance, and in this way, the IMD removes the error caused by the limited bandwidth of the amplifier. The IMD may then determine the tissue resistance based on the value of A. Also, if the value of N is two, then division by (N−1) may not be needed since two minus one is one.

While the foregoing describes steps and processes as being implemented by an IMD, it will be understood this is for illustration only. Described processes and steps may be performed in whole, or in part, by some other device or system, such as one or more processors that reside outside the body. Such processor(s) could be provided, for instance, by a clinician or patient programmer or by a separate server, workstation, and so on.

FIG. 1 is a conceptual diagram illustrating an example therapy system 10 that is configured to deliver therapy to patient 12 to manage a disorder of patient 12. Patient 12 ordinarily will be a human patient. In some cases, however, therapy system 10 may be applied to other mammalian or non-mammalian non-human patients. In the example shown in FIG. 1, therapy system 10 includes medical device programmer 14, implantable medical device (IMD) 16, lead extension 18, and one or more leads 20A and 20B (collectively "leads 20") with respective sets of electrodes 24, 26.

IMD 16 includes a stimulation generator configured to generate and deliver electrical stimulation therapy to one or more regions of brain 28 of patient 12 via one or more electrodes 24, 26 of leads 20A and 20B, respectively, alone or in combination with an electrode provided by outer housing 34 of IMD 16.

In the example shown in FIG. 1, therapy system 10 may be referred to as a DBS system because IMD 16 is configured to deliver electrical stimulation therapy directly to tissue within brain 28, e.g., a tissue site under the dura mater of brain 28 or one or more branches or nodes, or a confluence of fiber tracks. Frequency bands of therapeutic interest in DBS therapy may include the delta band (less than 4 Hz), the theta band (4-8 Hz), the alpha band (8-13 Hz), the beta band (13-35 Hz), the gamma band (35-100 Hz) and the high gamma band (100-400 Hz). In other examples, leads 20 may be positioned to deliver therapy to a surface of brain 28 (e.g., the cortical surface of brain 28). For example, in some examples, IMD 16 may provide cortical stimulation therapy to patient 12, e.g., by delivering electrical stimulation to one or more tissue sites in the cortex of brain 28. Frequency bands of therapeutic interest in cortical stimulation therapy may include the theta band, and the gamma band.

DBS may be used to treat or manage various patient conditions, such as, but not limited to, seizure disorders (e.g., epilepsy), pain, migraine headaches, psychiatric disorders (e.g., major depressive disorder (MDD), bipolar disorder, anxiety disorders, post traumatic stress disorder, dysthymic disorder, and obsessive compulsive disorder (OCD), behavior disorders, mood disorders, memory disorders, mentation disorders, movement disorders (e.g., essential tremor or Parkinson's disease), Huntington's disease, Alzheimer's disease, or other neurological or psychiatric disorders and impairment of patient 12. Therapy systems configured for treatment of other patient conditions via delivery of therapy to brain 28 can also be used in accordance with the techniques for determining one or more therapeutic windows disclosed herein.

In the example shown in FIG. 1, IMD 16 may be implanted within a subcutaneous pocket in the pectoral region of patient 12. In other examples, IMD 16 may be implanted within other regions of patient 12, such as a subcutaneous pocket in the abdomen or buttocks of patient 12 or proximate to the cranium of patient 12. Implanted lead extension 18 is coupled to IMD 16 via connector block 30 (also referred to as a header), which may include, for example, electrical contacts that electrically couple to respective electrical contacts on lead extension 18. The electrical contacts electrically couple the electrodes 24, 26 carried by leads 20 to IMD 16. Lead extension 18 traverses from the implant site of IMD 16, along the neck of patient 12 and through the cranium of patient 12 to access brain 28. IMD 16 can be constructed of a biocompatible material that resists corrosion and degradation from bodily fluids. IMD 16 may comprise a hermetic outer housing 34 to substantially enclose components, such as a processor, a therapy module, and memory.

In the example shown in FIG. 1, leads 20 are implanted within the right and left hemispheres, respectively, of brain 28 in order to deliver electrical stimulation to one or more regions of brain 28, which may be selected based on many factors, such as the type of patient condition for which therapy system 10 is implemented to manage. Other implant sites for leads 20 and IMD 16 are contemplated. For example, IMD 16 may be implanted on or within cranium 32 or leads 20 may be implanted within the same hemisphere at multiple target tissue sites or IMD 16 may be coupled to a single lead that is implanted in one or both hemispheres of brain 28.

During implantation of lead 16 within patient 12, a clinician may attempt to position electrodes 24, 26 of leads 20 such that electrodes 24, 26 are able to deliver electrical stimulation to one or more target tissue sites within brain 28 to manage patient symptoms associated with a disorder of patient 12. Leads 20 may be implanted to position electrodes 24, 26 at desired locations of brain 28 via any suitable technique, such as through respective burr holes in the skull of patient 12 or through a common burr hole in the cranium 32. Leads 20 may be placed at any location within brain 28 such that electrodes 24, 26 are capable of providing electrical stimulation to target therapy delivery sites within brain 28 during treatment.

The anatomical region within patient 12 that serves as the target tissue site for stimulation delivered by IMD 14 may be selected based on the patient condition. Different neurological or psychiatric disorders may be associated with activity in one or more of regions of brain 28, which may differ between patients. Accordingly, the target therapy delivery site for electrical stimulation therapy delivered by leads 20 may be selected based on the patient condition. For example, a suitable target therapy delivery site within brain 28 for controlling a movement disorder of patient 12 may include one or more of the pedunculopontine nucleus (PPN), thalamus, basal ganglia structures (e.g., globus pallidus, substantia nigra or subthalamic nucleus), zona inserta, fiber tracts, lenticular fasciculus (and branches thereof), ansa lenticularis, or the Field of Forel (thalamic fasciculus). The PPN may also be referred to as the pedunculopontine tegmental nucleus.

As another example, in the case of MDD, bipolar disorder, OCD, or other anxiety disorders, leads 20 may be implanted to deliver electrical stimulation to the anterior limb of the internal capsule of brain 28, and only the ventral portion of the anterior limb of the internal capsule (also referred to as a VC/VS), the subgenual component of the cingulate cortex (which may be referred to as CG25), anterior cingulate cortex Brodmann areas 32 and 24, various parts of the prefrontal cortex, including the dorsal lateral and medial pre-frontal cortex (PFC) (e.g., Brodmann area 9), ventromedial prefrontal cortex (e.g., Brodmann area 10), the lateral and medial orbitofrontal cortex (e.g., Brodmann area 11), the medial or nucleus accumbens, thalamus, intralaminar thalamic nuclei, amygdala, hippocampus, the lateral hypothalamus, the Locus ceruleus, the dorsal raphe nucleus, ventral tegmentum, the substantia nigra, subthalamic nucleus, the inferior thalamic peduncle, the dorsal medial nucleus of the thalamus, the habenula, the bed nucleus of the stria terminalis, or any combination thereof.

As another example, in the case of a seizure disorder or Alzheimer's disease, for example, leads 20 may be implanted to deliver electrical stimulation to regions within the Circuit of Papez, such as, e.g., one or more of the anterior thalamic nucleus, the internal capsule, the cingulate, the fornix, the mammillary bodies, the mammillothalamic tract (mammillothalamic fasciculus), or the hippocampus. Target therapy delivery sites not located in brain 28 of patient 12 are also contemplated.

Although leads 20 are shown in FIG. 1 as being coupled to a common lead extension 18, in other examples, leads 20 may be coupled to IMD 16 via separate lead extensions or directly coupled to IMD 16. Moreover, although FIG. 1 illustrates system 10 as including two leads 20A and 20B coupled to IMD 16 via lead extension 18, in some examples, system 10 may include one lead or more than two leads.

In the examples shown in FIG. 1, electrodes 24, 26 of leads 20 are shown as ring electrodes. Ring electrodes may be relatively easy to program and may be capable of delivering an electrical field to any tissue adjacent to leads 20. In other examples, electrodes 24, 26 of leads 20 may have different configurations. For example, one or more of the electrodes 24, 26 of leads 20 may have a complex electrode array geometry that is capable of producing shaped electrical fields, including interleaved stimulation. An example of a complex electrode array geometry may include an array of electrodes positioned at different axial positions along the length of a lead, as well as at different angular positions about the periphery, e.g., circumference, of the lead. The complex electrode array geometry may include multiple electrodes (e.g., partial ring or segmented electrodes) around the perimeter of each lead 20, in addition to, or instead of, a ring electrode. In this manner, electrical stimulation may be directed to a specific direction from leads 20 to enhance therapy efficacy and reduce possible adverse side effects from stimulating a large volume of tissue.

In some examples, outer housing 34 of IMD 16 may include one or more stimulation and/or sensing electrodes. For example, housing 34 can comprise an electrically conductive material, which forms a capacitive interface with the surrounding tissue, that is exposed to tissue of patient 12 when IMD 16 is implanted in patient 12. In other examples, leads 20 may have shapes other than elongated cylinders as shown in FIG. 1 with active or passive tip configurations. For example, leads 20 may be paddle leads, spherical leads, bendable leads, or any other type of shape effective in treating patient 12.

IMD 16 may deliver electrical stimulation therapy to brain 28 of patient 12 according to one or more therapy programs. A therapy program may define one or more electrical stimulation parameter values for therapy generated by a stimulation generator of IMD 16 and delivered from IMD 16 to a target therapy delivery site within patient 12 via one or more electrodes 24, 26. The electrical stimulation parameters may define an aspect of the electrical stimulation therapy, and may include, for example, voltage or current amplitude of an electrical stimulation signal, such as a voltage or current pulse amplitude, a frequency of the electrical stimulation signal, and, in the case of electrical stimulation pulses, a pulse rate, a pulse width, a waveform shape, and other appropriate parameters such as duration or duty cycle. In addition, if different electrodes are available for delivery of stimulation, a therapy parameter of a therapy program may be further characterized by an electrode combination, which may define electrodes 24, 26 selected for delivery of electrical stimulation and their respective polarities. In some examples, stimulation may be delivered using a continuous waveform and the stimulation parameters may define this waveform.

In addition to being configured to deliver therapy to manage a disorder of patient 12, therapy system 10 may be configured to sense bioelectrical brain signals of patient 12. For example, IMD 16 may include a sensing module that is configured to sense bioelectrical brain signals within one or more regions of brain 28 via a subset of electrodes 24, 26, another set of electrodes, or both. Accordingly, in some examples, electrodes 24, 26 may be used to deliver electrical stimulation from the therapy module to target sites within brain 28 as well as sense brain signals within brain 28. However, IMD 16 can also use a separate set of sensing electrodes to sense the bioelectrical brain signals. In some examples, the sensing module of IMD 16 may sense bioelectrical brain signals via one or more of the electrodes 24, 26 that are also used to deliver electrical stimulation to brain 28. In other examples, one or more of electrodes 24, 26 may be used to sense bioelectrical brain signals while one or more different electrodes 24, 26 may be used to deliver electrical stimulation.

Examples of bioelectrical brain signals include, but are not limited to, electrical signals generated from local field potentials (LFP's) within one or more regions of brain 28, such as, but not limited to, an electroencephalogram (EEG) signal or an electrocorticogram (ECoG) signal. In some examples, the electrical signals within brain 28 may reflect changes in electrical current produced by the sum of electrical potential differences across brain tissue.

External medical device programmer 14 is configured to wirelessly communicate with IMD 16 as needed to provide or retrieve therapy information. Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. In addition, or instead, programmer 14 may be a patient programmer that allows patient 12 to select programs and/or view and modify therapy parameter values. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that presents information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, then the buttons may be dedicated to performing a certain function, e.g., a power button, the buttons and the keypad may be soft keys that change in function depending upon the section of the user interface currently viewed by the user, or any combination thereof.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device that may run an application that enables the computing device to operate as a secure medical device programmer 14. A wireless adapter coupled to the computing device may enable secure communication between the computing device and IMD 16.

When programmer 14 is configured for use by the clinician, programmer 14 may be used to transmit programming information to IMD 16. Programming information may include, for example, hardware information, such as the type of leads 20, the arrangement of electrodes 24, 26 on leads 20, the position of leads 20 within brain 28, one or more therapy programs defining therapy parameter values, and any other information that may be useful for programming into IMD 16. Programmer 14 may also be capable of completing functional tests (e.g., measuring the impedance of electrodes 24, 26 of leads 20).

With the aid of programmer 14 or another computing device, a clinician may select one or more therapy programs for therapy system 10 and, in some examples, store the therapy programs within IMD 16. Programmer 14 may assist the clinician in the creation/identification of therapy programs by providing physiologically relevant information specific to patient 12.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or BLUETOOTH® specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

Therapy system 10 may be implemented to provide chronic stimulation therapy to patient 12 over the course of several months or years. However, system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

System 10 shown in FIG. 1 is merely one example of a therapy system for which therapeutic electrical stimulation parameters may be determined. The techniques described herein can be used to evaluate therapy programs for other therapy systems, such as therapy systems with other configurations of leads and electrodes, therapy systems with more than one IMD, and therapy systems including one or more leadless electrical stimulators (e.g., microstimulators having a smaller form factor than IMD 16 and which may not be coupled to any separate leads). The leadless electrical stimulators can be configured to generate and deliver electrical stimulation therapy to patient 12 via one or more electrodes on an outer housing of the electrical stimulator.

In some examples, IMD 16, programmer 14, or a user of programmer 14 determines the therapy parameters for the stimulation based on the tissue resistance at electrodes 24, 26. Tissue resistance at an electrode refers to the (spreading) resistance of the tissue from the electrode to ground. The ground node may be another electrode through which the current passes such as an electrode on lead 20A or 20B or an electrode on housing 34. In some examples, housing 34 may itself form the ground.

There may be various reasons for tissue resistance determination, such as for therapy programming. For instance, if the tissue resistance at one of electrodes 24, 26 is determined to be relatively high, then IMD 16, programmer 14, or the user may determine that a relatively high amplitude stimulation pulse is needed to reach the target stimulation area. As another example, IMD 16, programmer 14, or the user may control the amount of voltage or current delivered to each of electrodes 24, 26 for therapy field steering. To achieve the intended therapy field, IMD 16, programmer 14, or the user may determine the amount of voltage or current delivered to each of electrodes 24, 26 based on the determined tissue resistance at electrodes 24, 26.

In accordance with the techniques described in this disclosure, IMD 16 includes circuitry for determining the tissue resistance. For example, IMD 16 outputs a current via an electrode and determines the amount of voltage generated at the electrode due to the output of the current. IMD 16 or programmer 14 determines the tissue resistance by dividing the determined amount of voltage by the current. Although the above example describes IMD 16 outputting a current, in some examples, IMD 16 outputs a voltage via an electrode and determines the amount of current generated at the electrodes (e.g., the amount of current that flows through the electrode) due to the output of the voltage, and IMD 16 or programmer 14 determines the tissue resistance by dividing the voltage by the determined amount of current.

For ease of description, the techniques are described with IMD 16 outputting a current and determining a voltage. However, in general, IMD 16 may be considered as generating, at an electrode, an electrical signal of a first type (e.g., a voltage signal or a current signal) by outputting an electrical signal of a second type (e.g., a current signal if the generated signal is a voltage signal or a voltage signal if the generated signal is a current signal).

As described above, it may be undesirable for a DC current to flow through patient 12, and therefore the electrical signal that IMD 16 outputs should be a modulated signal that is modulated at a particular frequency. As one example, the electrical signal that IMD 16 outputs is a rectangular wave current signal with a certain frequency (e.g., 3.125 kHz).

An electrical signal having a rectangular waveform applied to the tissue coupled to the electrode would result in another electrical signal having a rectangular waveform (e.g., a current signal with a rectangular waveform applied to the tissue results in a generated voltage signal with a rectangular waveform, and vice-versa). This is because the tissue is mainly resistive and not reactive.

However, to ensure that DC current does not flow into patient 12, the signal path to one or more of electrodes 24, 26 each include a reactive component that blocks the DC current. For example, each signal path to electrodes 24, 26 includes a DC blocking capacitor. In this case, the capacitor adds reactance. Therefore, the signal that is generated from IMD 16 outputting the electrical signal is not a rectangular wave, but is a combination of a rectangular waveform and a triangular waveform.

For example, a current signal having a rectangular waveform flowing through the resistance of the tissue results in a voltage signal having a rectangular waveform, and the current signal having a rectangular waveform flowing through a capacitor results in a voltage signal having a triangular waveform. The rectangular waveform of the generated electrical signal is a function of the tissue resistance, and the triangular waveform of the generated electrical signal is a function of the reactance. In this disclosure, because the rectangular waveform of the generated electrical signal is a function of the resistivity of the tissue, the rectangular waveform may be referred to as the real-part of the generated electrical signal, and because the triangular waveform of the generated electrical signal is a function of the reactance of the reactive component, the triangular waveform may be referred to as the imaginary-part of the generated electrical signal.

To determine the tissue resistance, IMD 16 may remove the contribution of the imaginary-part from the generated signal, leaving the contribution of the real-part. One way in which to remove the contribution of the imaginary-part is to output the generated signal to a chopper circuit. In the techniques described in this disclosure, the chopper circuit operates at the same frequency as the frequency of the electrical signal that IMD 16 outputs.

A chopper circuit functions by multiplying an input signal by one for half a period, and negative one for the other half of the period. If the input to the chopper circuit is a rectangular wave, and the frequency of the chopper circuit is the same as that of the rectangular wave, then during the period where the rectangular wave is positive, the chopper circuit multiplies the rectangular wave by one. During the period where the rectangular wave is negative, the chopper circuit multiplies the rectangular wave by negative one, due to the frequency of the rectangular wave and frequency of the chopper circuit being the same.

By multiplying the rectangular wave by one when the rectangular wave is positive, and multiplying the rectangular wave by negative one when the rectangular wave is negative, the chopper circuit, in essence, keeps the positive portion of the rectangular wave the same and flips the negative portion of the rectangular wave into the positive portion. If the amplitude of the positive portion of the rectangular wave is the same as the negative portion of the rectangular wave, the output of the chopper circuit is a constant value.

For a triangular wave, the chopper circuit performs functions similar to those described for the rectangular wave. However, the output of the chopper circuit for an input triangular wave is not a constant value, and instead is a saw-tooth wave. The saw-tooth wave is positive for the same amount of time that it is negative (i.e., the saw-tooth wave includes no DC component).

The output of the chopper circuit may then be averaged by an averager circuit, which may be an analog circuit or a circuit including an A/D converter followed by a processor executing firmware to perform the averaging function. Averaging may include an integration operation and a division of the resulting integration by the amount of time used for the integration. For example, the A/D may be an integrator whose integration value is divided by the time over integration to determine an average value.

Because the saw-tooth wave is positive for the same amount of time that it is negative, the average of the saw-tooth wave is zero. However, in some cases, due to phase delay the average of the saw-tooth wave may not be zero. As described below, the error can be accounted for during manufacturing. The average of the constant value is the constant value. In this way, the averager circuit can be considered as removing the saw-tooth wave portion of the output from the chopper circuit, and maintains the constant value portion of the output from the chopper circuit. As described above, the constant value that the chopper circuit outputs is based on the real-part (i.e., rectangular wave) of the input to the chopper circuit, and the saw-tooth wave that the chopper circuit outputs is based on the imaginary-part (i.e., triangular wave) of the input to the chopper circuit. By averaging the output of the chopper circuit, the imaginary-part is removed (i.e., the saw-tooth wave is zeroed by the averaging or can be compensated for if not precisely zero) and the real-part is present (i.e., the average of the constant value is the constant value).

As also described above, the real-part of the input to the chopper circuit is proportional to the tissue resistance, and the imaginary-part of the input to the chopper circuit is proportional to the reactance. By averaging the output of the chopper circuit, the remaining constant value is proportional only to the tissue resistance, and IMD 16 or programmer 14 may determine the tissue resistance based on the constant value.

However, if the input to the chopper circuit is not a combination of a square wave and a triangular wave, then the output of the chopper circuit is not a combination of a constant value and a saw-tooth. For instance, the input of the chopper circuit is from the output of an amplifier, where the input to the amplifier is an electrical signal generated by the application of the voltage signal or current signal to electrodes 24, 26 for tissue resistance measurement.

Accordingly, the input to the amplifier is a combination of a rectangular wave (e.g., the portion of the electrical signal that is proportional to the tissue resistance, also referred to as the real-part of the electrical signal) and a triangular wave (e.g., the portion of the electrical signal that is proportional to the reactance, also referred to as the imaginary-part of the electrical signal). Due to limited bandwidth of the amplifier, the amplifier may not output a combination of a rectangular wave and a triangular wave. Rather, the amplifier may output a combination of a trapezoidal wave and a triangular-like wave with sinusoidal transitions from a negative slope to a positive slope, and vice-versa.

For instance, a rectangular wave includes a very high slew rate (i.e., very fast rising and falling edges), and the amplifier may not be capable of outputting signals with such a high slew rate. Therefore, rather than a transition from a high to a low or vice-versa being virtually instantaneous, as would be the case in a rectangular wave, the transition from high to low or vice-versa in the output of the amplifier takes longer, resulting in a more trapezoidal wave. For similar reasons, the triangular wave portion of the electrical signal that the amplifier receives results in a triangular-like wave with sinusoid transitions from a negative slope to a positive slope, and vice-versa, because of the inability of the amplifier to perform immediate transitions from a negative slope to a positive slope, and vice-versa, due to the bandwidth limitations. The trapezoidal wave and triangular-like wave together form an intermediate electrical signal that is then processed to determine the tissue resistance.

In this case, the output of the chopper circuit for the trapezoidal wave portion may not be a constant value, and the output of the chopper circuit for the triangular-like wave portion may not be a saw-tooth. Although the result of chopping the triangular-like wave portion is not a saw-tooth, but saw-tooth-like, the resulting wave may still be positive for the same amount of time that it is negative (or approximately the same amount of time). Therefore, the averager circuit may still average this saw-tooth-like wave to zero, or approximately zero. Some calibration may be needed because the average may not be zero.

For the resulting wave from the chopping of the trapezoidal wave portion, the averager circuit may output an average value. However, this average value may be different than the constant value that the averager circuit would output if the output of the amplifier had been a more ideal rectangular wave. For example, assume that the output of the averager circuit for the case where the input to the chopper circuit is a combination of the rectangular wave and the triangular wave is a first average value, and the output of the averager circuit for the case where the input to the chopper circuit is a combination of a trapezoidal wave and a triangular-like wave is a second average value. In this example, the second average value equals the first average value plus an error value, where the error value is due to the input to the chopper circuit including a trapezoidal wave, rather than a rectangular wave. There may be little to no effect of the input to the chopper circuit including a triangular-like wave, rather than a triangular wave.

In the above example, the "first average value" would be the result had the input to the chopper circuit included a rectangular wave, rather than a trapezoidal wave, where the trapezoidal wave exists due to the bandwidth limitations of the amplifier. Therefore, the "first average value" is proportional to the tissue resistance, whereas the "second average value" includes an error value. The techniques described in this disclosure describe ways to reduce or eliminate the "error value."

For instance, the error value is proportional to the frequency of the electrical signal. The greater the frequency of the electrical signal, the greater the error value in the output of the averager circuit will be, and the lower the frequency of the electrical signal, the lower the error value in the output of the averager circuit will be. As described in more detail below, the techniques described in this disclosure may exploit the relationship between the frequency of the electrical signal and the error value to remove or reduce the error value from the output of the averager circuit.

In some examples, the trapezoidal wave does not have the same rise and fall time as the rectangular wave, but rather slowly rises to a settling high voltage or slowly falls to a settling low voltage. The period of the electrical signal should be long enough to allow the trapezoidal wave to reach the settling high voltage or to fall to the settling low voltage. In this disclosure, the error value of the impedance measurement is proportional to the area difference between the rectangular wave and the trapezoidal wave that reaches its settling high or low voltages. The difference between the rectangular wave and the trapezoidal wave that reaches its settling high or low voltages (e.g., the error value in the tissue resistance) is a function of the frequency. By determining the impedance at different frequencies, IMD 16 or programmer 14 may subtract out the error value to determine a more accurate tissue resistance.

For example, IMD 16 or programmer 14 may determine multiple output values from the averager circuit for different electrical signals generated at different frequencies. Because the error value in each output of the averager circuit is proportional to the frequencies of the respective electrical signals, the ratio between the frequencies and the ratio between the error values may be approximately equal. IMD 16 or programmer 14 may utilize the ratio between the frequencies to determine by how much to add to or subtract from one of the values outputted by the averager circuit to remove the error value. After the error value from the output of the averager circuit is removed, the resulting value is proportional to the tissue resistance. In this manner, IMD 16 and/or programmer 14 may determine the value proportional to the tissue resistance, and then determine the tissue resistance based on the value proportional to the tissue resistance.

Figure 2:
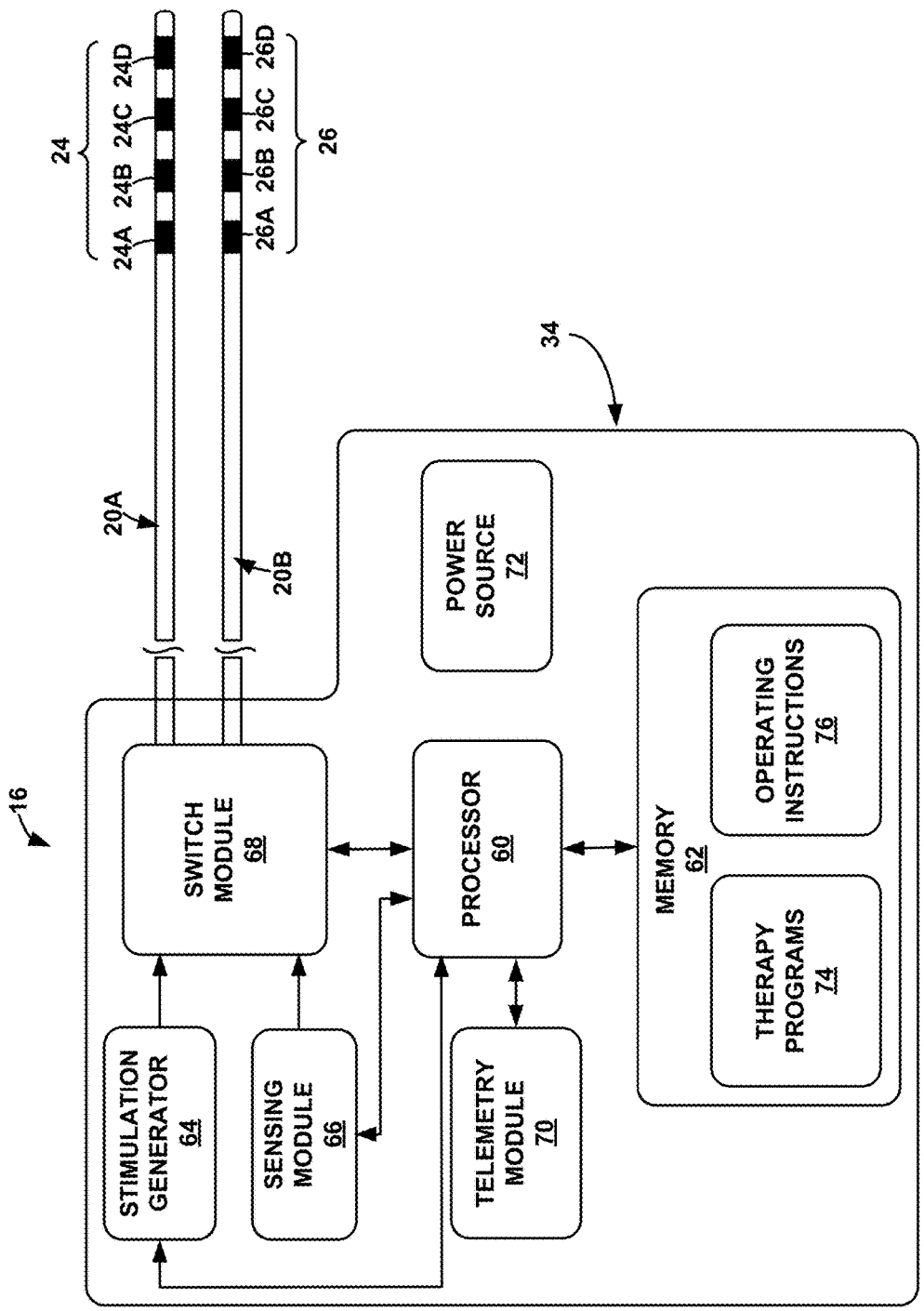
FIG. 2 is functional block diagram illustrating components of an example medical device.

FIG. 2 is functional block diagram illustrating components of an example IMD 16. In the example shown in FIG. 2, IMD 16 includes processor 60, memory 62, stimulation generator 64, sensing module 66, switch module 68, telemetry module 70, and power source 72. Memory 62, as well as other memories described herein, may include any volatile or non-volatile media, such as a random access memory (RAM), read only memory (ROM), non-volatile RAM (NVRAM), electrically erasable programmable ROM (EEPROM), flash memory, and the like. Memory 62 may store computer-readable instructions that, when executed by processor 60, cause IMD 16 to perform various functions described herein.

In the example shown in FIG. 2, memory 62 stores therapy programs 74 and operating instructions 76, e.g., in separate memories within memory 62 or separate areas within memory 62. Each stored therapy program 74 defines a particular program of therapy in terms of respective values for electrical stimulation parameters, such as an electrode combination, current or voltage amplitude, and, if stimulation generator 64 generates and delivers stimulation pulses, the therapy programs may define values for a pulse width and pulse rate of a stimulation signal. The stimulation signals delivered by IMD 16 may be of any form, such as stimulation pulses, continuous-wave signals (e.g., sine waves), or the like. Operating instructions 76 guide general operation of IMD 16 under control of processor 60, and may include instructions for monitoring brain signals within one or more brain regions via electrodes 24, 26 and delivering electrical stimulation therapy to patient 12.

Stimulation generator 64, under the control of processor 60, generates stimulation signals for delivery to patient 12 via selected combinations of electrodes 24, 26. In some examples, stimulation generator 64 generates and delivers stimulation signals to one or more target regions of brain 28 (FIG. 1), via a select combination of electrodes 24, 26, based on one or more stored therapy programs 74. The target tissue sites within brain 28 for stimulation signals or other types of therapy and stimulation parameter values may depend on the patient condition for which therapy system 10 is implemented to manage.

The processors described in this disclosure, including processor 60, may include one or more digital signal processors (DSPs), general purpose microprocessors, application specific integrated circuits (ASICs), field programmable logic arrays (FPGAs), or other equivalent integrated or discrete logic circuitry, or combinations thereof. The functions attributed to processors described herein may be provided by a hardware device and embodied as software, firmware, hardware, or any combination thereof. Processor 60 is configured to control stimulation generator 64 according to therapy programs 74 stored by memory 62 to apply particular stimulation parameter values specified by one or more therapy programs.

In the example shown in FIG. 2, the set of electrodes 24 of lead 20A includes electrodes 24A, 24B, 24C, and 24D, and the set of electrodes 26 of lead 20B includes electrodes 26A, 26B, 26C, and 26D. Processor 60 may control switch module 68 to apply the stimulation signals generated by stimulation generator 64 to selected combinations of electrodes 24, 26. In particular, switch module 68 may couple stimulation signals to selected conductors within leads 20, which, in turn, deliver the stimulation signals across selected electrodes 24, 26. Switch module 68 may be a switch array, switch matrix, multiplexer, or any other type of switching module configured to selectively couple stimulation energy to selected electrodes 24, 26 and to selectively sense bioelectrical brain signals with selected electrodes 24, 26. Hence, stimulation generator 64 is coupled to electrodes 24, 26 via switch module 68 and conductors within leads 20. In some examples, however, IMD 16 does not include switch module 68. For example, IMD 16 may include multiple sources of stimulation energy (e.g., current sources).

Stimulation generator 64 may be a single channel or multi-channel stimulation generator. In particular, stimulation generator 64 may be capable of delivering a single stimulation pulse, multiple stimulation pulses or continuous signal at a given time via a single electrode combination or multiple stimulation pulses or waveforms at a given time via multiple electrode combinations. In some examples, however, stimulation generator 64 and switch module 68 may be configured to deliver multiple channels on a time-interleaved basis. For example, switch module 68 may serve to time divide the output of stimulation generator 64 across different electrode combinations at different times to deliver multiple programs or channels of stimulation energy to patient 12.

Sensing module 66, under the control of processor 60, is configured to sense bioelectrical brain signals of patient 12 via a selected subset of electrodes 24, 26 or with one or more electrodes 24, 26 and at least a portion of a conductive outer housing 34 of IMD 16, an electrode on outer housing 34 of IMD 16 or another reference. Processor 60 may control switch module 68 to electrically connect sensing module 66 to selected electrodes 24, 26. In this way, sensing module 66 may selectively sense bioelectrical brain signals with different combinations of electrodes 24, 26 (and/or a reference other than an electrode 24, 26). Although sensing module 66 is incorporated into a common housing 34 with stimulation generator 64 and processor 60 in FIG. 2, in other examples, sensing module 66 is in a separate outer housing from outer housing 34 of IMD 16 and communicates with processor 60 via wired or wireless communication techniques.

Telemetry module 70 is configured to support wireless communication between IMD 16 and an external programmer 14 or another computing device under the control of processor 60. Processor 60 of IMD 16 may receive, as updates to programs, values for various stimulation parameters from programmer 14 via telemetry module 70. The updates to the therapy programs may be stored within therapy programs 74 portion of memory 62. Telemetry module 70 in IMD 16, as well as telemetry modules in other devices and systems described herein, such as programmer 14, may accomplish communication by RF communication techniques. In addition, telemetry module 70 may communicate with external medical device programmer 14 via proximal inductive interaction of IMD 16 with programmer 14. Accordingly, telemetry module 70 may send information to external programmer 14 on a continuous basis, at periodic intervals, or upon request from IMD 16 or programmer 14.

Power source 72 delivers operating power to various components of IMD 16. Power source 72 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

In some example, the therapy parameters stored as part of therapy programs 74 are based on the tissue resistance at electrodes 24, 26. The tissue resistance is the resistance from the tissue coupled to one of electrodes 24, 26 to ground, where one example of the ground is the case of IMD 16 (i.e., outer housing 34). The tissue may not include any reactive components; hence, the term tissue "resistance," rather than "impedance."

The tissue resistance may affect the amplitude of the therapy parameters, as one example. For instance, if the target area to be stimulated is located in a relatively high resistance area of patient 12, the amplitude of the therapy parameters may be selected to be higher than if the target area to be stimulated were located in a relatively low resistance area of patient 12. For instance, in a current based stimulation system, the actual stimulation field, or V-field, is determined mostly by the resistive properties of the tissue, with the tissue resistance of the target area determining the shape of the realized stimulation V-field. Accordingly, in some examples, processor 60 may be configured to determine the tissue resistance of the tissue coupled to electrodes 24, 26.

As one example, switch module 68 may include tissue resistance circuitry needed for determining values that processor 60 uses to determine the tissue resistance. It should be understood that, in some examples, rather than or in addition to processor 60 determining the tissue resistance, programmer 14 may determine the tissue resistance based on the values determined by circuitry within switch module 68. Also, the tissue resistance circuitry used to determine the tissue resistance need not necessarily reside within switch module 68, and may be external or otherwise separate from switch module 68.

Processor 60 may determine one impedance matrix Z, where the impedance matrix Z is a two dimensional matrix of tissue resistance values for each of electrodes 24 of lead 20A, and another impedance matrix Z, where this matrix is a two dimensional matrix of tissue resistance values for each of electrodes 26 on lead 20B. To generate the impedance matrix Z, processor 60 may cause switch module 68 to output an electrical signal (e.g., excitation signal) via one of electrodes 24 (e.g., electrode 24A), and determine the tissue resistance at electrode 24A and determine the tissue resistance values at electrodes 24B-24D when the electrical signal is outputted by electrode 24A. The resulting values form the first column in the impedance matrix Z. Next, processor 60 causes switch module 68 to output an electrical signal via electrode 24B, and determines the tissue resistance at electrode 24B and determines the tissue resistance values at electrodes 24C-24D (and optionally 24A) when the electrical signal is outputted by electrode 24B. The resulting values form the second column in the impedance matrix Z. Processor 60 may repeat these steps to determine the resistance values at electrode 24C, and 24A, 24B and 24D when the electrical signal is outputted at electrode 24C, and determine the resistance value at electrodes 24D and at electrodes 24A-24C, when the electrical signal is outputted via electrode 24D.

At the conclusion of this process, processor 60 may have determined half of the values of impedance matrix Z for lead 20A. For example, for a two-dimensional matrix, assume there is a diagonal line from the left-top of the matrix to the bottom-right of the matrix. Using the above techniques, processor 60 may have determined the tissue resistance values for the bottom portion of this hypothetical diagonal bisecting line. The tissue resistance values for the top portion of this hypothetical diagonal bisecting line may be the mirror of the bottom portion. In this manner, processor 60 may determine the impedance matrix Z for lead 20A, and implement similar techniques to determine the impedance matrix Z for lead 20B.

For example, the resistance measurement on the electrode on which the excitation signal is outputted makes the diagonal resistance measurement in the impedance matrix Z. The resistance measurement on the other electrodes based on the excitation signal is referred to as a transresistance and fills in the rest of the resistance Z matrix.

One way for the resistance measurement circuitry to determine the impedance matrix Z is to inject a small-signal sinusoidal AC current (e.g., AC current with relatively low amplitude) into each of lead electrode 24, and measure the resulting voltage magnitude on all electrodes of interest (e.g., electrodes 24). The division of the measured voltage with the current equals the magnitude of the resistance. However, due to parasitic capacitance and any DC blocking capacitors in the signal path to electrodes 24, 26B, the values in the impedance matrix Z include a real-part (Re(Z)) and an imaginary-part (Im(Z)). The magnitude of the values in the impedance matrix Z may be substantially equal to only the real-part if the value of the imaginary-part is minimized. In other words, by minimizing the affect of the parasitic capacitance and any DC blocking capacitors, the determined impedance matrix Z may be substantially equal to the tissue resistance.

To minimize the affect of the parasitic capacitance and any DC blocking capacitors, the resistance measurement circuitry may output the current at a frequency that is sufficiently high so that the real-part Re(Z) dominates the measured magnitude, but not so high because, otherwise, parasitic capacitance increases the contribution of the imaginary-part Im(Z). However, there may be drawbacks to such a technique for determining tissue resistance. For example, the optimal frequency range for determining the impedance matrix Z depends on the resistivity of the tissue itself. If lead 20A is placed in a low-ohmic region (e.g., relatively low resistive area), the resistance measurement circuitry may need to output an AC current at a high frequency, and outputting current at such a high frequency may be impractical (i.e., the frequency region where resistance dominates the measured impedance shifts to high frequencies for the low-ohmic region). Conversely, if lead 20A is placed in a high-ohmic region (e.g., relatively high resistive area), parasitic capacitors may dominate the magnitude of the values of the impedance matrix Z, reducing the accuracy of the estimation of the real-part of the value.

Furthermore, relying on the magnitude of determined values of the impedance matrix Z may at best be an estimation of the actual tissue resistance. For cases where a more precise tissue resistance measurement is appropriate, it may be possible that no frequency range of the AC current exists to provide a sufficiently precise tissue resistance determination.

In accordance with the techniques described in this disclosure, the resistance measurement circuitry may not rely on the magnitude of the determined impedance to estimate the tissue resistance. Rather, the resistance measurement circuitry may remove the imaginary-part, so that only the real-part is left. In this manner, the techniques described in this disclosure provide for a way to measure the real matrix (Re(Z)) directly without the drawbacks of the estimating tissue resistance from the magnitude of the Z values. The techniques may be used robustly and independently of the actual measured tissue resistance with low-frequency current or voltage injection sources. In other words, the techniques described in this disclosure can be utilized for any tissue location, and at a relatively low frequency that the resistance measurement circuitry can generate.

In the above examples, the bandwidth limitation of the amplifier causes an error value in the resistance measurement. However, one additional cause of the error value could be the input range of the amplifier. Therefore, if the techniques described in this disclosure are not used, the amplifier would need to be a high bandwidth amplifier with a wide input range that the amplifier can amplify without overloading. With the techniques described in this disclosure, the error value can be removed without needing an amplifier having a high bandwidth and wide input range.

As described in more detail, the frequency of a current signal or voltage signal that the resistance measurement circuitry outputs (i.e., the injection source frequency of the excitation signal) is compatible with the power-efficient and low-noise instrumentation amplifiers typically used in neural recording front-ends (i.e., the techniques described in this disclosure may utilize amplifiers already in an existing system, rather than needing additional amplifiers, for the tissue resistance measurement). Accordingly, the resistance measurement circuitry may be integrated into switch module 68 without much additional power or hardware overhead. The resistance measurement circuitry may be coupled to the lines that connect to electrodes 24, 26 for the tissue resistance measurement, and may be used to determine the tissue resistance without requiring too much additional power or additional components.

As described in more detail below, the resistance measurement circuit includes at least one electrical signal source, an amplifier, a chopper circuit, and an averager circuit. The output of an electrical signal of a first type (e.g., a current signal), via one of electrodes 24, 26 (e.g., electrode 24A) by the at least one electrical signal source, generates an electrical signal of a second type (e.g., a voltage signal) at the input of the amplifier. For instance, the at least one electrical signal source may output a current signal having a rectangular waveform (i.e., a rectangular wave current signal). The reactance of the parasitic capacitance and the DC blocking capacitor, and the tissue resistance coupled to electrode 24A result in a voltage signal forming at the input of the amplifier. This voltage signal includes a real-part from the tissue resistance, and an imaginary-part from the reactance component. The real-part of the input voltage signal provided to the amplifier may be a rectangular wave (i.e., a rectangular wave input voltage signal), and the imaginary-part of the input voltage signal to the amplifier may be triangular wave (i.e., a triangular wave input voltage signal).

The output of the amplifier is an electrical signal having a real-part and an imaginary-part, and referred to as an intermediate electrical signal. Assuming the bandwidth of the amplifier is extremely high, the real-part of the amplifier output would be a rectangular wave, and the imaginary-part of the amplifier output would be a triangular wave. The chopper circuit, functioning at the same frequency as the frequency of the electrical signal outputted by the at least one electrical signal source, converts the rectangular wave portion outputted by the amplifier to a constant value, and converts the triangular wave portion outputted by the amplifier to a saw-tooth wave, where the average of the saw-tooth wave is zero (i.e., the saw-tooth wave includes no DC component). The averager circuit averages the output of the chopper circuit. The result is that the constant value portion of the output of the chopper circuit remains, and the sawtooth portion of the output of the chopper circuit averages out to close to zero (the difference if not zero can be determined during manufacturing). In this way, the final resulting value is proportional only to the tissue resistance, and the contribution from the parasitic and DC blocking capacitance is removed.

In other words, utilizing a chopper circuit and an averager circuit for tissue resistance may be based on the observation that the response of resistors (e.g., tissue resistance) and capacitors (e.g., parasitic, tissue interface, or DC blocking) is different when an AC current excitation is applied. This difference can be used to remove the capacitor response (i.e., the imaginary-part) from the measurement signal (i.e., the voltage signal) so that only the resistive response of interest remains.

However, the amplifier may not have sufficient bandwidth to output an electrical signal having a rectangular wave or a triangular wave. For such cases, the amplifier may output an electrical signal that includes a trapezoidal wave and a triangular-like wave (e.g., intermediate electrical signal). The chopper circuit may output a first jagged waveform for the trapezoidal wave input, and a second jagged waveform for the triangular-like wave input. The averager circuit may output an average value that is different than the value the averager circuit would have outputted had the output of the amplifier included a rectangular wave and a triangular wave. In other words, the average value outputted by the averager circuit equals the value outputted by the averager circuit for the rectangular wave scenario plus an error value.

In the techniques described in this disclosure, by determining average values with different frequencies for the electrical signal that the at least one electrical signal source outputs, processor 60 may be able to determine a value that is proportional to the tissue resistance, and remove the error value and the contribution from the parasitic and DC blocking capacitance. For example, the error value is proportional to the frequency of the electrical signal outputted by the at least one electrical source. In this case, the difference in the average values at the different frequencies may be proportional to the ratio of the different frequencies used to generate the average values. Utilizing techniques described in more detail herein, processor 60 may utilize the ratio between the different frequencies to remove the error value from one of the average values, resulting in a value that is proportional only to the tissue resistance. Processor 60 may then determine the tissue resistance from the resulting value.

In other words, utilizing multiple average values for tissue resistance measurement relates to power-efficient improvements to the accuracy of the tissue resistance measurement. Each measurement (e.g., average value) includes an error caused by the finite settling speed of the amplifier (e.g., the bandwidth limitations). If two subsequent measurements are performed, at two different current excitation frequencies (i.e., the frequency of the rectangular wave of the current signal), the dominant settling error in both measurements can be removed to improve the tissue resistance measurement accuracy without needing a fast-settling and power hungry front-end (e.g., without needing a high bandwidth, high power amplifier). As noted above, this error may be removed if the trapezoidal wave has enough time to settle (e.g., the frequency is not too fast and the trapezoidal wave has enough time to reach its final value).

The example illustrated in FIG. 2 is one example way in which the techniques described in this disclosure may be implemented. However, the techniques described in this disclosure are not so limited.

Figure 3:
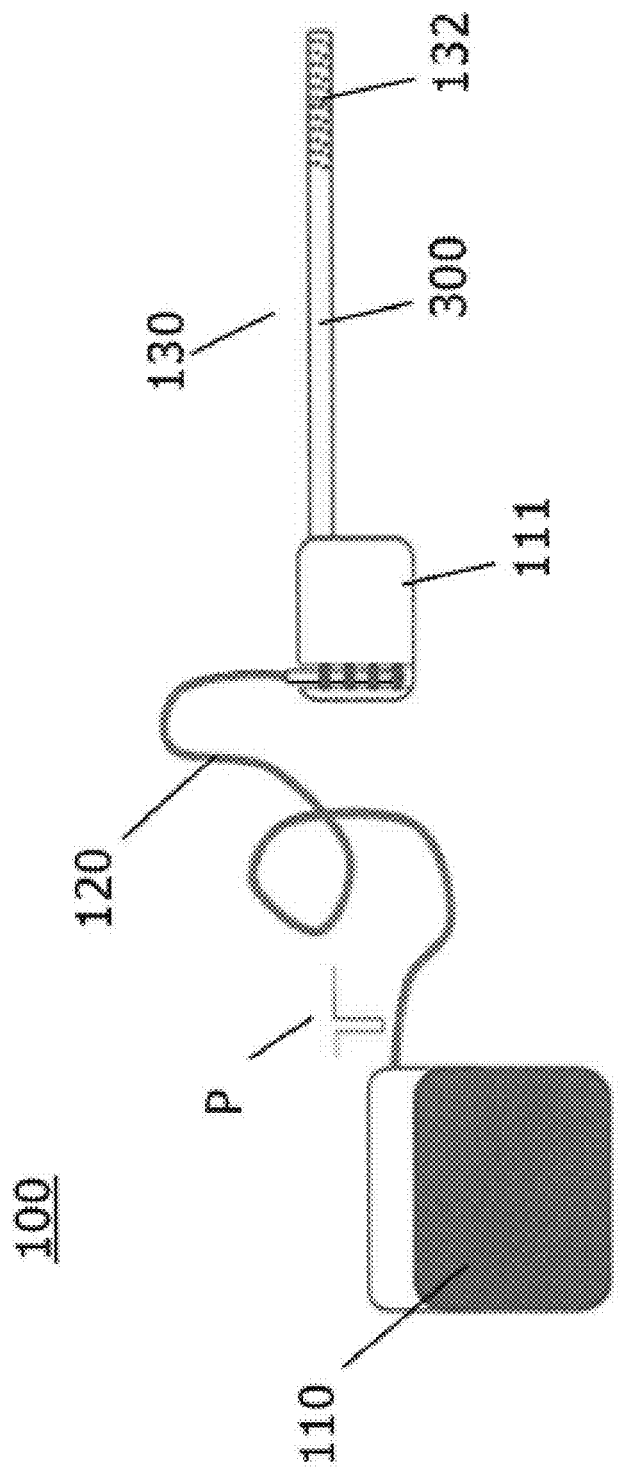
FIG. 3 is a functional block diagram illustrating components of an example medical device system.

FIG. 3 is a functional block diagram illustrating components of an example medical device system. For example, FIG. 3 shows schematically and in greater detail an example of a system for brain applications, here for neurostimulation and/or neurorecording as a deep brain stimulation system. As illustrated, probe system 100 comprises at least one probe 130 for brain applications with stimulation and/or recording electrodes 132 (e.g., 40 electrodes 132 can be provided on outer body surface at the distal end of the probe 130). By means of the extension wire 120, pulses P supplied by controller 110 (e.g., stimulation pulses) can be transmitted to the active lead can (ALC) 111. The controller 110 can be an implantable pulse generator (IPG) 110. In other words, IPG 110, illustrated in FIG. 3, is another example of IMD 16.

Figure 4:
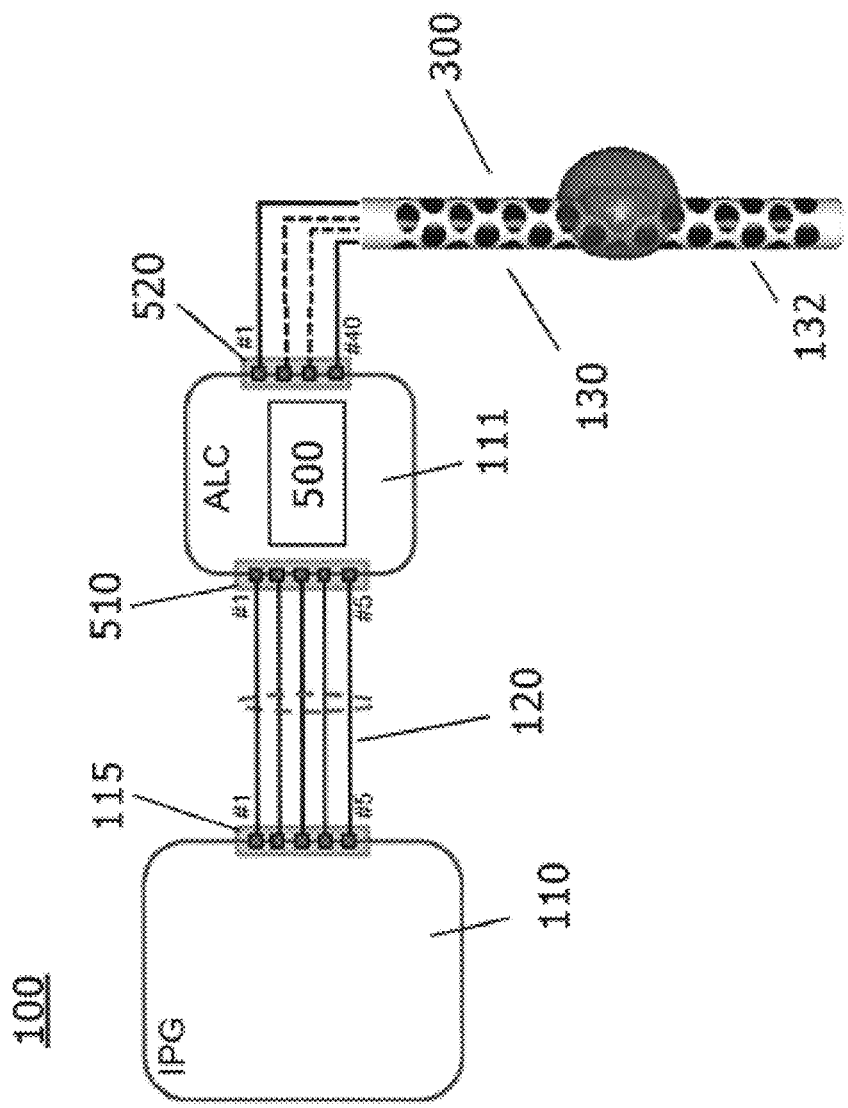
FIG. 4 is a functional block diagram illustrating components of another example medical device system.

FIG. 4 is a functional block diagram illustrating components of another example medical device system. For example, FIG. 4 shows a schematic drawing of a system for brain applications according to one example of an electronic module 500. The electronic module 500 is in this example integrated into the active lead can 111.

System 100 of FIG. 4 having a DBS probe 130 as defined above comprises an IPG 110 and an active lead can 111 with an array of electronic switches that connects electrodes 132 arranged at the distal end of the lead 300 with the pulse generator lines of the IPG 110 either directly or indirectly through logic in the active lead can 111 and/or in the IPG 110. In addition, IPG 110 includes neural recording facilities. IPG 110 and active lead can 111 may be connected through an interface cable 120 which may include for example, five lines. Accordingly, the IPG 110 has a 5-pin connector 115 which is connected to active lead can 111 via the interface cable 120.

In one example, interface cable 120 comprises multiple cables including a lead extension that couples at a proximal end to the LCFX connector 115 of IPG 110, and which terminates in a distal end connector (not shown in FIG. 4). This distal end connector couples to a corresponding proximal end connector carried by a cable that extends from, but is not selectively connectable/disconnectable to/from active lead can 111. In an alternative example, interface cable 120 may comprise a single cable having a proximal end connector that couples to connector 115 of IPG 110 and a distal end connector that couples to 5-pin LCFX connector 510 of the active lead can 111.

The active lead can 111 comprises a multi-pin connector with a 5-pin LCFX connector 510 for the interface cable 120 and a 40-pin connector 520 for the lead 300. It is mechanically possible to design these two feed-through connectors 510, 520 with a high pin density to reduce the area of the active lead can 111 significantly. However, this area advantage may only materialize if the electrical components of the active lead can 111 are shrunk in similar proportions as the feed-through connectors 510, 520. Moreover, a very thin active lead can 111, most desirable to reduce its impact on skin erosion, may need a high pin density, but also a reduction in the height of both feedthrough pins 511, 521 and interior electrical components. Thus, both the electronics volume and area of the active lead can 111 are miniaturized to realize a small active lead can 111. Note that techniques to shrink the active lead can 111 can also be applied to the implantable pulse generator 110, or any other implant module, for example, to trade for an increase in battery life time and/or increased functionality.

In accordance with the techniques described in this disclosure, active lead can 111 of FIGS. 4 and 5 may be configured to implement the tissue resistance techniques described in this disclosure. For example, active lead can 111 may include the resistance measurement circuitry of at least one electrical signal source, an amplifier, a chopper circuit, and an averager circuit as described above, and IPG 110 or active lead can 111 may include a processor, like processor 60 of FIG. 2, for the tissue resistance determination.

As described above, the parasitic capacitance affects the tissue resistance measurement. This parasitic capacitance, formed by the electrode-tissue interface, as well as the DC blocking capacitor, may impact the tissue resistance measurement more when small electrodes, such as electrodes 132, are formed on probe 130. Moreover, active lead can 111 may be a relatively miniaturized module, and therefore, there may be limited space for DC blocking capacitors. This may result in needing low capacitance DC blocking capacitors, leading to relatively low block capacitance per electrode. In the techniques described in the disclosure, the effects of the parasitic capacitance and the DC blocking capacitors are removed, leading to an accurate tissue resistance measurement, which may otherwise have been impacted by the parasitic capacitance and the capacitance from the DC blocking capacitors.

Furthermore, leads 20A and 20B are one example of leads that can be utilized for therapy delivery and sensing. However, the techniques described in this disclosure are not so limited.

Figure 5A:
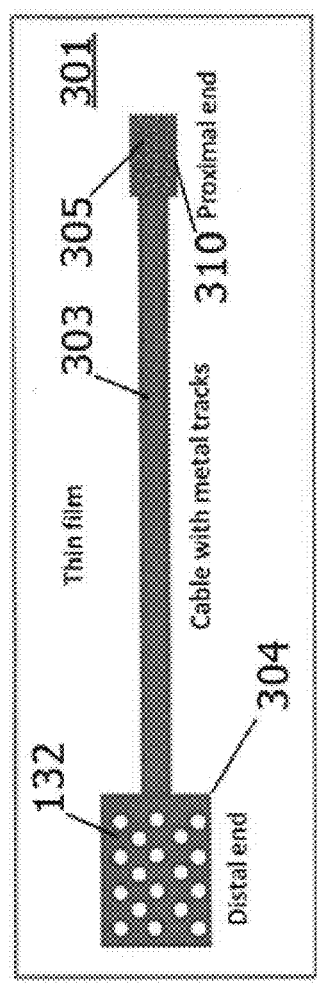
FIGS. 5A-5C illustrate examples of probes for stimulation and/or sensing.
Figure 5B:
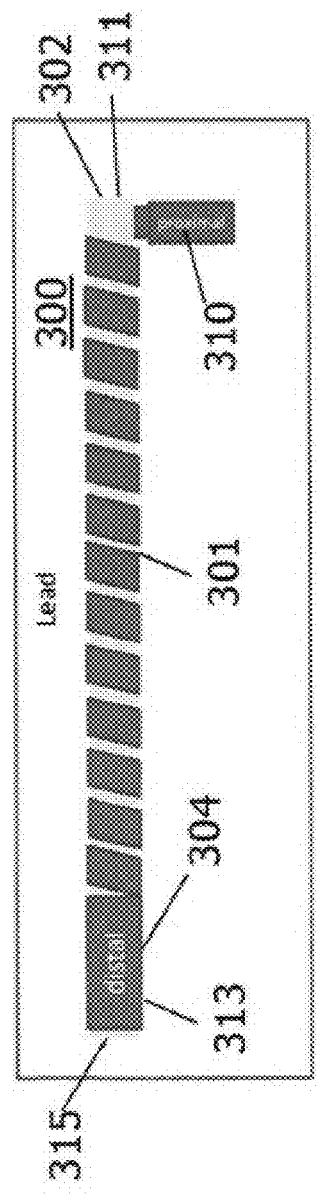
Figure 5C:
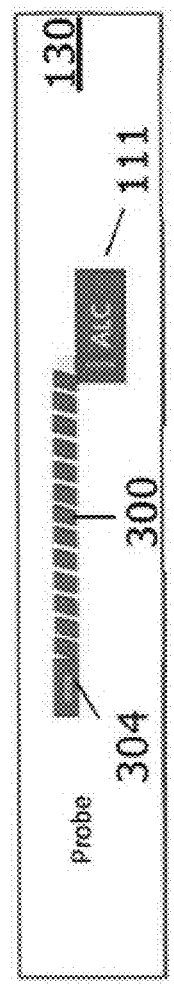

FIGS. 5A-5C illustrate examples of probes for stimulation and/or sensing. Relative to FIGS. 5A and 5B, FIG. 5C further illustrates a typical architecture for a Deep Brain Stimulation probe 130 that comprises a DBS lead 300 and an active lead can 111 comprising electronic means to address electrodes 132 on the distal end 304 of the thin film 301, which is arranged at the distal end 313 and next to the distal tip 315 of the DBS lead 300, as illustrated in FIG. 5B. The lead 300 comprises a carrier 302 for a thin film 301, the carrier 302 providing the mechanical configuration of the DBS lead 300 and the thin film 301. The thin film 301 may include at least one electrically conductive layer, such as one made of a biocompatible material. The thin film 301 is assembled to the carrier 302 and further processed to constitute the lead 300. The thin film 301 for a lead may be formed by a thin film product having a distal end 304, a cable 303 with metal tracks and a proximal end 310, as illustrated in FIG. 5A. The proximal end 310 of the thin film 301 arranged at the proximal end 311 of the lead 300 is electrically connected to the active lead can 111. The active lead can 111 comprises the switch matrix of the DBS steering electronics. In some examples, active lead can 111 may further comprise a signal generator that is in addition to, or instead of, a pulse/signal generator provided by IPG 110. This signal generator of active lead can 111 may provide a signal to control stimulation delivered via electrodes 132.

The distal end 304 of thin film 301 comprises the electrodes 132 for the brain stimulation. The proximal end 310 comprises the interconnect contacts 305 for each metal line in the cable 303. The cable 303 comprises metal lines (not shown) to connect each distal electrodes 132 to a designated proximal contact 305.

Figure 6:
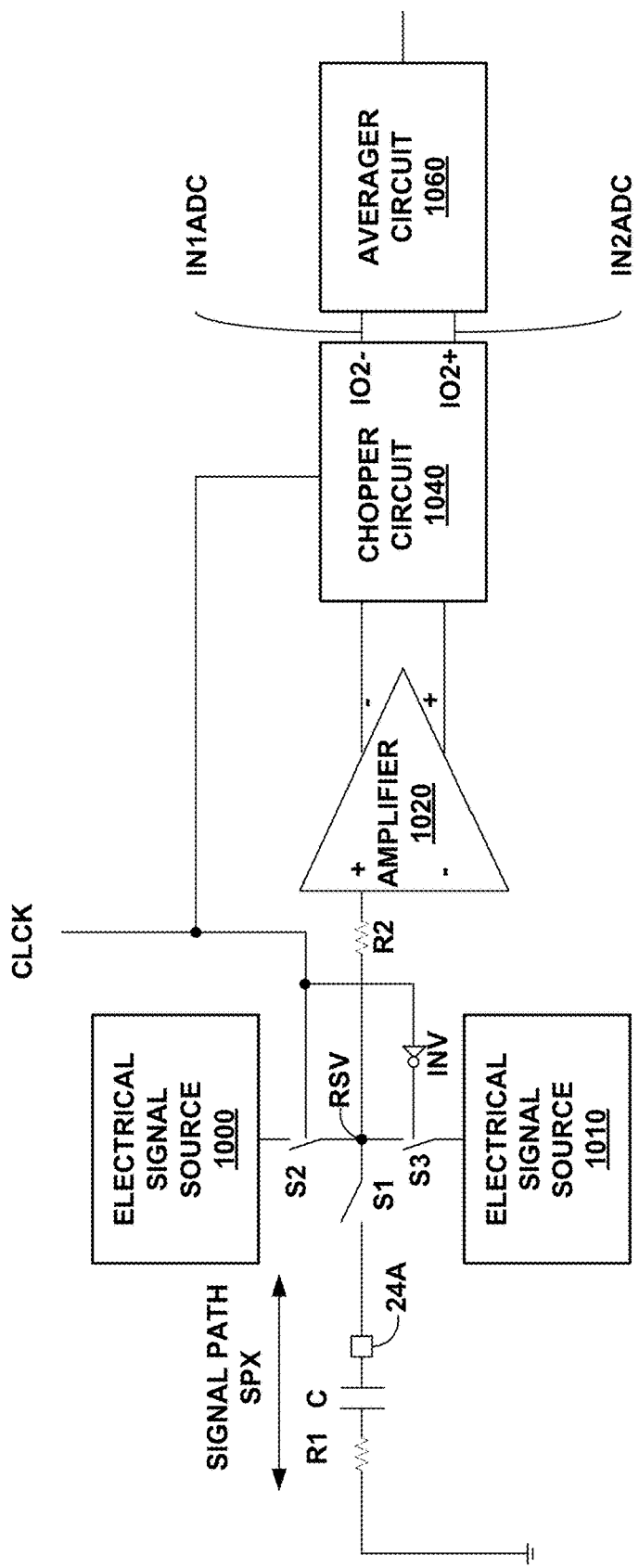
FIG. 6 is a functional block diagram illustrating components of a resistance measurement circuitry.

FIG. 6 is a functional block diagram illustrating components of a resistance measurement circuitry. The resistance measurement circuitry includes electrical signal source 1000 and 1010, switches S2 and S3, inverter INV, resistor R2, amplifier 1020, chopper circuit 1040, and averager circuit 1060. The components of the resistance measurement circuitry may be formed as an integrated circuit, and may be an ASIC that is part of switching module 68. However, the techniques described in this disclosure are not so limited, and this logic may be separate components, combined in different ways, and need not necessarily be part of switching module 68. For instance, in the example of FIG. 4, some or all of these components may reside within active lead can.

In FIG. 6, the signal path SPX refers to the way in which stimulation therapy flows out of electrode 24A, and the way in which sensed electrical signals enter via electrode 24A. For ease of illustration, the connection to switch module 68 and the way in which the output from stimulation generator 64 flows to electrode 24A or the way in which the sensed electrical signals are received by sensing module 66 is not illustrated. The signal path SPX includes a simplified model of one of a plurality of signal paths that can be coupled to stimulation generator 64 or sensing module 66 through a switch matrix (e.g., switch module 68) or ALC. When switch S1 is closed, stimulation is outputted or sensed electrical signals are provided.

Each signal path SPX relates to one electrode (e.g., electrode 24A is illustrated in FIG. 6). Accordingly, there are for example, forty signal paths SPX, in examples where there are forty electrodes on a probe (e.g., as in FIG. 4) or four signal paths SPX (e.g., one for each of electrodes 24A-24D). For ease of illustration, the circuitry for only electrode 24A is illustrated, with the understanding that similar techniques may be used for tissue resistance determination for the other electrodes. It should be understood that the techniques described in this disclosure are applicable to other types of electrodes as well. As one example, the electrode that is part of the housing of IMD 16 may also be used as an electrode for implementing the example techniques. In general, any conductive component on IMD 16 may be used for performing the example techniques described in this disclosure.

The resistance R1 represents all the resistance between switch module 68 (e.g., switch matrix resistance of switch module 68, lead track resistance, which is resistance of the wire or bus within lead that connects to the electrode, and the tissue resistance itself) and a chosen return terminal (e.g., ground via housing 34 and/or housing of ALC 111). The capacitor C is formed by the total series capacitance (e.g., DC blocking capacitor and electrode-tissue interface capacitance) in the loop.

The resistance measurement circuitry includes two electrical signal sources (e.g., electrical signal source 1000 and electrical signal source 1010), supplying respective constant currents I1 and I2. In some examples, electrical signal source 1000 and 1010 may supply constant voltages. The example is illustrated with respect to electrical signal sources 1000 and 1010 supplying constant currents. The amplitude of the output of electrical signal source 1000 and 1010 may be approximately the same, but it may be possible for the amplitudes to differ. Although not illustrated, a control loop, such as a DC servo loop, may control the amplitudes of electrical signal source 1000 and 1010 so that the amplitudes are kept to be the same.

Electrical signal source 1000 is coupled in series with switch S2 to node RSV (response signal voltage). Electrical signal source 1010 is coupled in series with switch S3 to node RSV. In this example, electrical signal sources 1000 and 1010 together implement a push-pull current source mutually supplying currents I1 and I2 to the signal path SPX if switch S1 is closed. Switches S2 and S3 are controlled by control signal ΦCH (referred to as CLCK) which is a clock signal that alternately opens and closes switches S2 and S3 (i.e., switch S3 receives the inverse of the signal to switch S2 via inverter INV). Accordingly, either current I1 or current I2 flow through signal path SPX and out of electrode 24A, when current I1 is flowing, and into electrode 24B, when current I2 is flowing. The magnitudes of currents I1 and I2 may be equal (I1=I2=I0).

The stimulus or excitation signal (e.g., the electrical signal generated by electrical signal sources 1000 and 1010) is a rectangular wave current signal alternating around a ground level (for example analog ground, system ground or virtual ground) with a positive amplitude and a negative amplitude of I0. The excitation signal may not include any DC content. In other words, the push-pull excitation generates a DC neutral periodic rectangular-wave current. For example, current I1 flows out of electrode 24A, and current I2 flows in through electrode 24A. Therefore, equal amounts of current flows out of electrode 24A in one direction and into electrode 24A in the other direction. In this case, current I1 can be considered as a positive current and current I2 can be considered as a negative current, meaning that there is no DC component in the current flowing through patient tissue.

The alternating frequency may be an order of magnitude larger than the typical stimulation frequencies for the neural application. For example, the frequency of the CLCK signal may be much larger than the frequency of neural application (e.g., 3.125 kHz or greater as merely one non-limiting example). In some examples, processor 60 may provide the CLCK signal; however, a component other than processor 60 may provide the CLCK signal. The amplitude I0 (e.g., the amplitude of the current signals outputted by electrical signal sources 1000 and 1010) is advantageously far below the currents typically used to stimulate neural tissue. As described above, this excitation current is injected via the switch module 68 or a switch matrix in ALC 111 of which only a single switch S1 is shown. This switch S1 connects to a series combination of a resistance R1 and a capacitor C including all the resistance and capacitance of the signal path SPX.

If the signal path SPX is excited with an alternating current excitation signal (e.g., electrical signal sources 1000 and 1010 output an electrical signal of a second type), the response signal on node RSV is a voltage signal (e.g., an electrical signal of a first type). Node RSV is coupled to an input of amplifier 1020. In some examples, amplifier 1020 is an instrumentation amplifier, such as an operational transconductance amplifier (OTA). In examples where amplifier 1020 is an OTA, amplifier 1020 converts the voltage signal at its input into a current signal.

It should be understood that amplifier 1020 is described as an OTA, as merely on example. In some examples, amplifier 1020 may be an amplifier that does not convert the voltage signal into a current signal, and is a voltage amplifier that outputs an amplified voltage signal. As another example, in examples where electrical signal sources 1000 and 1010 generate a rectangular wave voltage signal, amplifier 1020 may receive as input a current signal. In such cases, amplifier 1020 may covert the current signal into a voltage signal, or keep the current signal, and output an amplified current signal.

Amplifier 1020 may be a high resistance input so that the output of electrical signal sources 1000 and 1010 does not flow into amplifier 1020, but instead through the tissue. Amplifier 1020 may convert the RSV voltage and covert it into a differential output current (however, a differential system is not needed and provided as one example). Amplifier 1020 may provide gain to the current or voltage input to amplifier 1020, may be a unity gain amplifier (e.g., gain of 1), or may reduce the amplitude (e.g., provide less than 1 gain so that the output is smaller than the input).

In a possible configuration, input resistor R2 is coupled to the positive input of amplifier 1020. In the example illustrated in FIG. 6, amplifier 1020 amplifies (or unity gain or less than unity gain) the voltage signal generated on node RSV and, in case of an OTA, converts the signals into output currents IO1− and IO1+. Amplifier 1020 may convert the generated voltage signal into a current signal because it can be advantageous to process currents in the following stages (e.g., in chopper circuit 1040) because the averager is used as integrator and it is easier to implement the integrator as an on-chip capacitor. If voltages were used, an inductor would be needed for integration, and forming an inductor on chip may not be possible requiring the inductor to be off chip.

Figure 7:
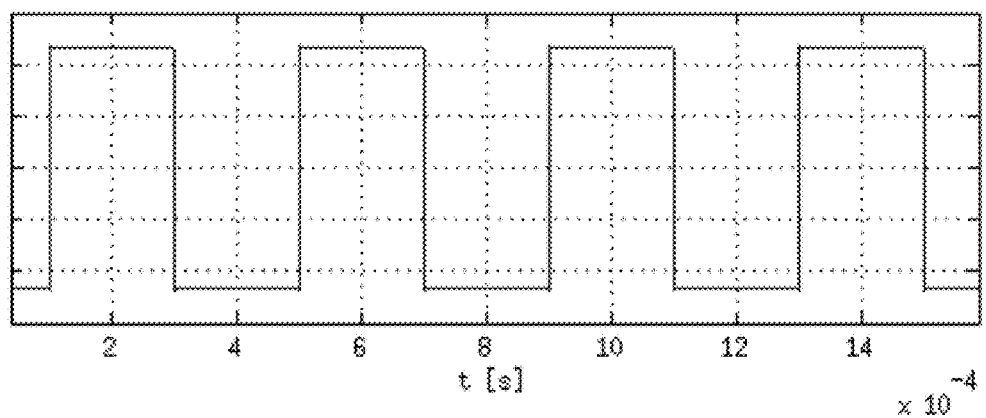
FIG. 7 is a graphical diagram illustrating the rectangular wave portion of the electrical signal formed at an input of an amplifier used for tissue resistance measurement.

As illustrated in FIG. 6, amplifier 1040 can have a symmetrical architecture (e.g., fully differential). In other words, the rectangular-wave current flowing through the resistance R1 of the signal path SPX introduces a rectangular-wave voltage component, as illustrated in FIG. 7 and described in more detail below, in the signal measured by amplifier 1020. This same excitation current is integrated by the series capacitance C and this adds a triangular waveform component, illustrated in FIG. 8 and explained in more detail below, to the signal measured by amplifier 1020. The voltage signal at the input of amplifier 1020 (e.g., the voltage signal that includes the rectangular waveform component and the triangular waveform component) has no DC component.

Chopper circuit 1040 is coupled to the output(s) of amplifier 1020. The frequency at which chopper circuit 1040 operates may be the same as the frequency of the excitation current. For example, as illustrated, the clock signal CLCK that controls switches S2 and S3 is the same clock signal that controls the operation of chopper circuit 1040. In this way, the same frequency that is used for the alternating signal supplied by electrical signal sources 1000 and 1010 is used for chopper circuit 1040.

Figure 13:
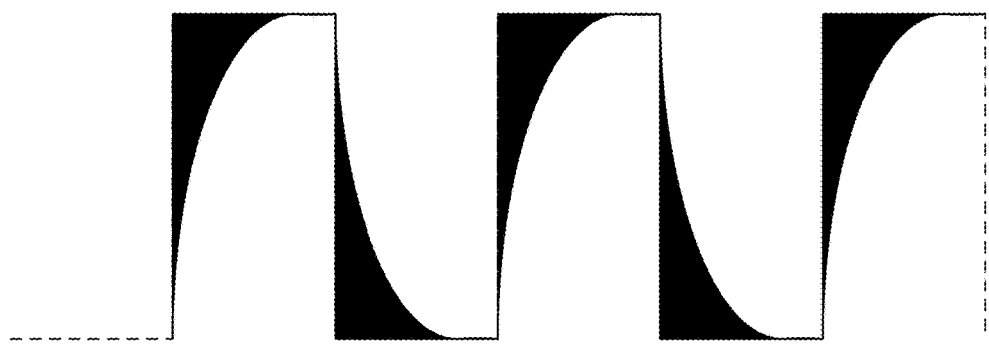
FIG. 13 is a graphical diagram illustrating the trapezoidal wave portion of the electrical signal formed at an output of an amplifier used for tissue resistance measurement.
Figure 14:
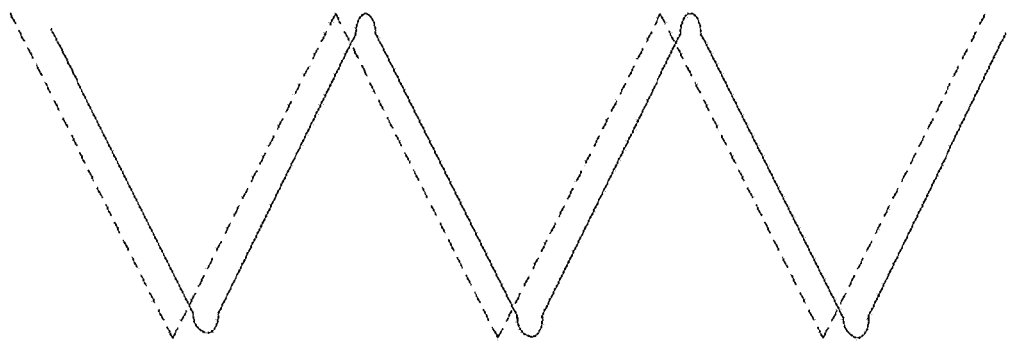
FIG. 14 is a graphical diagram illustrating the triangular wave portion of the electrical signal formed at an output of an amplifier used for tissue resistance measurement.

The output signals of chopper circuit 1040 are signals IO2−, IO2+, which may be currents, and in some examples, symmetric currents. Averager circuit 1060 is coupled to the output of chopper circuit 1040 for receiving the output signal(s) IO2−, IO2+ of chopper circuit 1040 at input terminals IN1ADC, IN2ADC, respectively. Output signal(s) IO2−, IO2+ form intermediate electrical signal that outputs to chopper circuit 1040. An example of the intermediate signal having the trapezoidal wave and triangular like wave is illustrated in FIGS. 13 and 14, respectively.

Averager circuit 1060 may be an analog-to-digital converter (ADC), and is an averaging and/or integrating ADC. However, averager circuit 1060 need not necessarily be an ADC in every example. Averaging generally increases the signal-to-noise ratio (SNR) of the ADC. In the techniques described in this disclosure, the averaging configuration of averager circuit 1060 positively affects the errors and noise produced by the previous stages (amplifier 1020 and chopper circuit 1040) as some of these errors and/or artifacts are eliminated by averager circuit 1060. Averager circuit 1060 may perform the averaging in an analog or in a digital manner. In general, averager circuit 1060 may average by summing up several samples and dividing the sum by the amount of samples. For example, averager circuit 1060 may perform an integration operation over a known time (e.g., a set number of periods) and dividing by the time over which the integration was performed.

In general, the amplifier 1020 amplifies its input voltage into a current (OTA) which is subsequently chopped, by chopper circuit 1040, at the same frequency as the excitation source changes from current source I1 to current source I2. To chop the output of amplifier 1020, chopper circuit 1040 multiplies the current signal received from amplifier 1020 by one for half a period of the CLCK clock signal, and multiplies the current signal received from amplifier 1020 by negative one for the other half period of the CLCK clock signal.

The result of chopper circuit 1040 multiplying the rectangular wave of the current signal by one for half period, and by negative one for the other half period, results in a DC current component because one multiplied by the amplitude of positive part of the rectangular wave, which is half the period, results in the amplitude of the rectangular wave, and negative one multiplied by the amplitude of the negative part of the rectangular wave, which is the other half of the period, results in the same amplitude of the rectangular wave (i.e., negative one multiplied by a negative value is a positive value).

Therefore, the ADC of averager circuit 1060 digitizes a DC current component (illustrated in FIG. 9), which is the result of the chopped instrumentation amplifier rectangular-wave output current, and a superimposed saw-tooth component (illustrated in FIG. 10), which is the result of the chopped amplified triangular current wave. The averaging by averager circuit 1060 results in only the DC current at the input giving rise to a digital code DOUT at the output of averager circuit 1060, while the saw tooth, whose DC content is zero, is effectively eliminated by the averaging (e.g., integrating action) of averager circuit 1060. Thus the digital output code is representative of the measured resistance, and therefore, the real parts Re(Z) of the impedance matrix Z of all the signal paths can directly be measured by the techniques described in this disclosure when all electrodes 132, 24, or 26 of interest are scanned one after another.

It should be noted that if chopper circuit 1040 and electrical signal sources 1000 and 1010 are disabled, the same architecture can be used as neural recording channel. In other words, amplifier 1020 may be the same amplifier as that used for sensing signals, and a new, separate amplifier is not needed. Moreover, when the bandwidth of the amplifier 1020 in neural recording mode is too low for the excitation current frequency (typically in the kHz range), amplifier 1020 can be programmed to have a larger, but still relatively small, bandwidth during resistance measurement. In this manner, the architecture illustrated in FIG. 6 together with the automatic programming of the ALC switch matrix via built-in state machines enables the direct measurement of the real part Re(Z) of the impedance matrix Z.

However, if the bandwidth of amplifier 1020 is limited (e.g., for a low-cost, low-power option), the output of amplifier 1020 may not be a combination of a rectangular wave current and a triangular wave current. Rather, the output of amplifier 1020 may be a combination of a trapezoidal wave current and a triangular-like wave current.

Moreover, the impact of the small-bandwidth, but power-efficient amplifier 1020 on the achievable measurement accuracy can largely be eliminated by the measurements of the resistance at two different frequencies f1 (e.g., 1 kHz to 100 kHz) and f2 (e.g., 10 kHz to 100 kHz). However, f1 and f2 should not be considered limited to these example frequency ranges. Processor 60 may then be configured to vary the control signal ΦCH between a first frequency f1 and a second frequency f2. In some examples, these two frequencies f1 and f2 may be relatively close together. In this way, the errors due to insufficient settling (limited bandwidth) of amplifier 1020 and/or other stages can be eliminated.

To eliminate the errors from the limited bandwidth of amplifier 1020, processor 60 may be configured to determine multiple average values (e.g., two average values) by generating multiple electrical signals (e.g., two electrical signals) at different frequencies (e.g., f1 and f2). For example, electronic signal sources 1000 and 1010 may output, via electrode 24A, a first current signal at a first frequency, causing a first voltage signal to be generated at the input of amplifier 1020. Again, it should be noted that rather than outputting a current, it may be possible to output a voltage, which causes a current to be generated at the input of amplifier 1020. For purposes of example, the techniques are described with respect to a current being outputted, with the understanding that the techniques function the same with a voltage being outputted.

The resistance measurement circuitry may process this first voltage signal. For example, processing this first voltage signal includes amplifier 1020 amplifying the first voltage signal, chopper circuit 1040 chopping the output of amplifier 1020 (e.g., the chopping the intermediate electrical signal), and averager circuit 1060 averaging the output of chopper circuit 1040 to generate a first output signal (e.g., a first average value). In this example, the first average value equals a value proportional to the tissue resistance plus a first error value that is proportional to the first frequency.

Then, electronic signal sources 1000 and 1010 may output, via electrode 24A, a second current signal at a second frequency, causing a second voltage signal to be generated at the input of amplifier 1020. Amplifier 1020, chopper circuit 1040, and averager circuit 1060 may process this second voltage signal to generate a second output signal (e.g., second average value). In this example, the second average value equals a value proportional to the tissue resistance plus a second error value that is proportional to the second frequency.

Because the first error value is proportional to the first frequency, and the second error value is proportional to the second frequency, the ratio of the first frequency to the second frequency equals the ratio of the first error value to the second error value (i.e., second frequency divided by first frequency equals second error value divided by first error value). For example, assume that the second frequency divided by the first frequency equals N (i.e., f2/f1=N). Accordingly, the second error value divided by the first error value also equals N (i.e., second error value/first error value=N). The second error value therefore equals N multiplied by the first error value (i.e., second error value=N*first error value).

As described above, the equations for the first average value and second average value are:

first average value=value proportional to tissue resistance+first error value;

second average value=value proportional to tissue resistance+second error value.

By substituting N*first error value for the second error value, the equation for the second average value can be rewritten as:

second average value=value proportional to tissue resistance+N*first error value.

In this case, there are now two equations and two unknowns (e.g., first average value and second average value are known from the output of averager circuit 1060, the value of N is known because processor 60 sets the first frequency and second frequency, and the value proportional to tissue resistance and the first error value are unknown). By multiplying the equation for the first average value by N, the resulting equation is:

$N*$first average value=$N*$value proportional to tissue resistance+$N*$first error value.

Processor 60 may subtract the equation for the second average value from the above equation for N*first average value. In equation form, processor 60 may determine:

$N*$first average value−second average value=
($N*$value proportional to tissue resistance+
$N*$first error value)−(value proportional to tissue resistance+$N*$first error value).

The above equation can be rewritten as:

$N*$first average value−second average value=
($N*$value proportional to tissue resistance−value proportional to tissue resistance)+($N*$first error value−$N*$first error value).

The result of the above equation is:

$N*$first average value−second average value=$(N-1)$
*value proportional to tissue resistance.

The above equation can then be rewritten as:

$(N*$first average value−second average value$)/(N-1)$
=value proportional to tissue resistance.

Because N, the first average value, and the second average value are known, by multiplying the first average value by the ratio between the first excitation frequency and the second excitation frequency, subtracting the second average value from the result of the multiplication, and dividing the result of the subtract by (N−1), processor 60 may determine a value that is proportional to the tissue resistance, and the error value is removed from the measurement. Processor 60 may then determine the tissue resistance at electrode 20A based on the value that is proportional to the tissue resistance. For example, if a current is applied, and the measured signal is a voltage (e.g., the value proportional to tissue resistance), the tissue resistance is equal to the voltage divided by the current. In some examples, if the ratio between the first and second frequencies is 2 (i.e., N=2), then processor 60 may multiply the first average value by 2 and subtract the second average value to determine the value proportional to the tissue resistance.

FIG. 7 is a graphical diagram illustrating the rectangular wave portion of the electrical signal formed at an input of an amplifier used for tissue resistance measurement. For example, FIG. 7 is a simplified representation of the waveform of the real part of a response signal received in the example illustrated in FIG. 6. The shown response signal is received on node RSV if the signal path SPX is excited by electronic signal sources 1000 and 1010, in particular a push-pull current source as previously described. The real part is generated by the resistance RX of signal path SPX which is mainly due to the resistance of the tissue. The real part is a rectangular wave voltage signal alternating between the positive voltage V0=RX*I0 (for I1=I0) and −V0=−RX*IO (for I2=I0) around ground level (0V), where RX is the tissue resistance.

For example, the rectangular-wave current flowing through the resistance R of the tissue introduces a rectangular-wave voltage component, as shown in FIG. 7, in the signal measured by amplifier 1020. In this manner, a push-pull excitation source (e.g., electronic signal sources 1000 and 1010) generates a DC neutral periodic rectangular-wave current whose frequency is an order of magnitude larger than the typical stimulation frequencies and whose amplitude is far below the currents typically used to stimulate neural tissue. This excitation current is injected via a switch matrix (which may reside within switch module 68 in the example of FIG. 2 or may reside within active lead can 111 in the example of FIG. 4) of which only a single switch is shown in FIG. 6. This switch connects to a series combination of a resistance R and a capacitor C. The resistance R represents all the resistance between the excitation current source (e.g. switch matrix resistance, lead track resistance and the tissue resistance itself and in some cases resistance of extension wire 120) and a chosen return terminal (e.g. IPG and/or ALC housing), while the capacitor C is formed by the total series capacitance (mainly DC blocking capacitor and electrode-tissue interface capacitance) in the loop.

Figure 8:
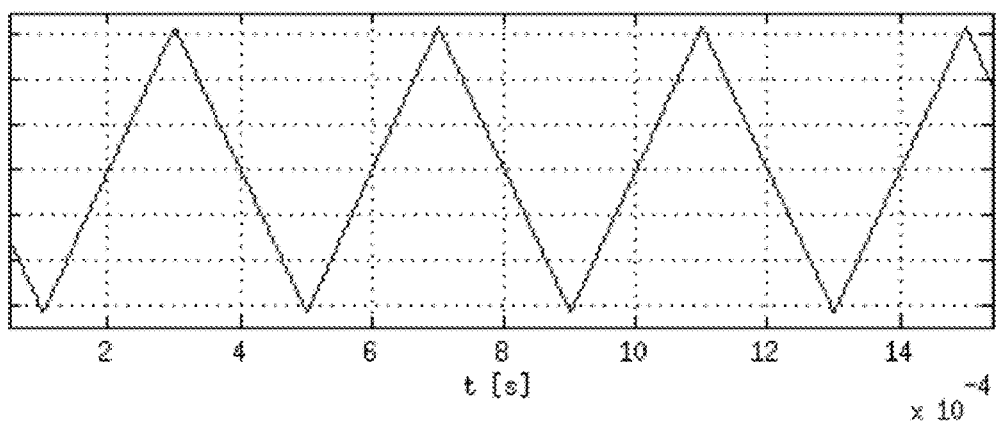
FIG. 8 is a graphical diagram illustrating the triangular wave portion of the electrical signal formed at an input of an amplifier used for tissue resistance measurement.

FIG. 8 is a graphical diagram illustrating the triangular wave portion of the electrical signal formed at an input of an amplifier used for tissue resistance measurement. For example, FIG. 8 is a simplified representation of the waveform of the imaginary part of a response signal received in the example in FIG. 6. As described above, the same excitation current used to generate the rectangular wave portion illustrated in FIG. 7 is integrated by the series capacitance C and this adds a triangular waveform component, illustrated in FIG. 8, to the signal measured by amplifier 1020. The triangular wave includes no DC component. For example, due to the push/pull configuration of electrical signal source 1000 and electrical signal source 1010, there is no DC in the triangular wave.

As described above, amplifier 1020 amplifies its input voltage into a current (OTA) which is subsequently chopped by chopper circuit 1040 at exactly the same frequency as the excitation current source. Therefore, the analog-to-digital converter (ADC) of averager circuit 1060 digitizes a DC current component, which is the result of the chopped instrumentation amplifier rectangular-wave output current and a superimposed saw tooth component, which is the result of the chopped amplified triangular current wave.

Figure 9:
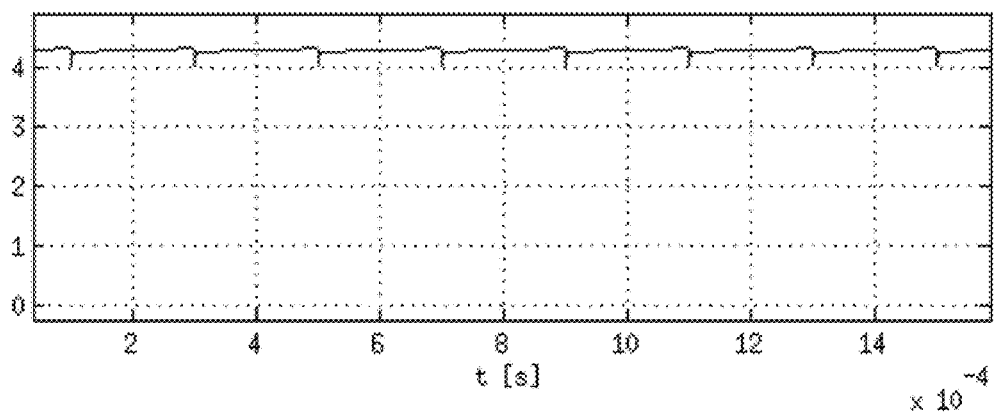
FIG. 9 is a graphical diagram illustrating a DC current component that is proportional to the tissue resistance generated from chopping the rectangular wave illustrated in FIG. 7.
Figure 10:
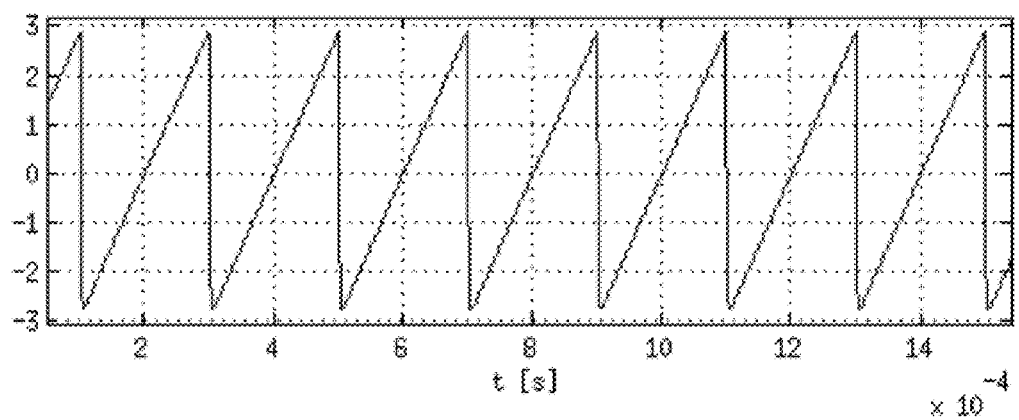
FIG. 10 is a graphical diagram illustrating a saw-tooth wave that is proportional to the reactance in the signal path.

FIG. 9 is a graphical diagram illustrating a DC current component that is proportional to the tissue resistance generated from chopping the rectangular wave illustrated in FIG. 7. FIG. 9 is a simplified representation of the waveform of the real part after chopping of a response signal received in the example of FIG. 7. FIG. 10 is a graphical diagram illustrating a saw-tooth wave that is proportional to the reactance in the signal path. FIG. 10 is a simplified representation of the waveform of the imaginary part after chopping of a response signal received in the example of FIG. 8.

Averager circuit 1060 is an averaging analog-to-digital converter (ADC), which implies that only the DC current at the ADC's input gives rise to a digital code at its output, while the saw tooth, whose DC content is zero, is effectively eliminated by the integrating action of the averaging ADC of averager circuit 1060. Thus the digital output code is representative of the measured tissue resistance, and therefore, the real part Re(Z) of the complete impedance matrix Z can directly be measured by this architecture when all electrodes of interest are scanned one after another (e.g., apply excitation signal on one electrode, determine resistance on that electrode and transresistance on all other electrodes, then apply excitation signal on another electrode, determine resistance on that electrode and transresistance on all other electrodes, and so forth for each electrode). Also, if chopper circuit 1040 and excitation current sources (e.g., electrical signal sources 1000 and 1010) are disabled, the same architecture can be used as a neural recording channel. Moreover, when bandwidth of amplifier 1020 in neural recording mode is too low for the excitation current frequency (typically in the kHz range), it can be programmed to have a larger, but still relatively small, bandwidth during resistance measurement.

Figure 11:
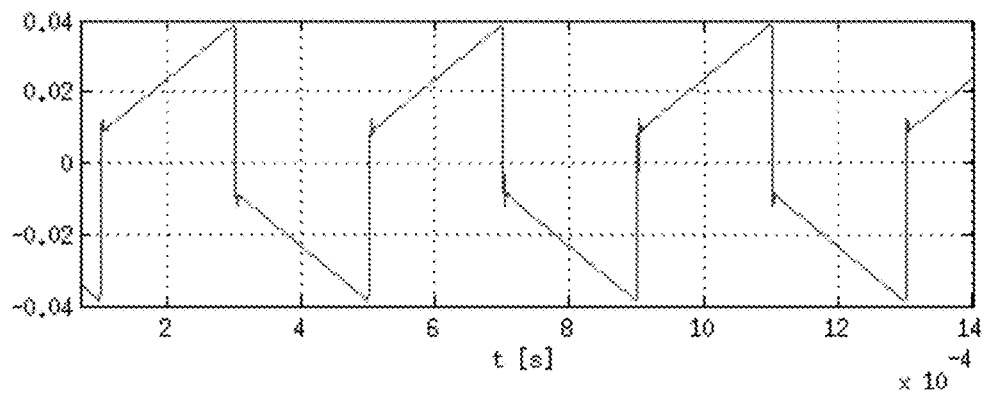
FIG. 11 is a graphical diagram illustrating the electrical signal at the input of the amplifier.
Figure 12:
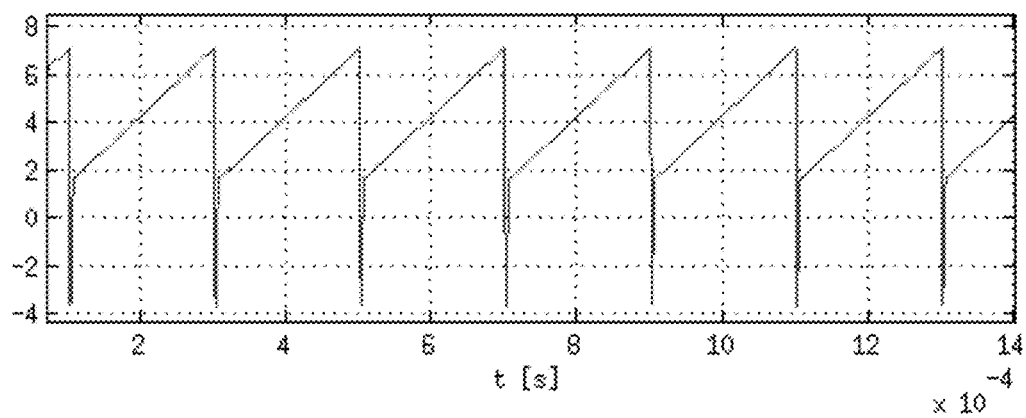
FIG. 12 is a graphical diagram illustrating the output of a chopper circuit when the input is the wave illustrated in FIG. 11.

FIG. 11 is a graphical diagram illustrating the electrical signal at the input of the amplifier. For instance, FIG. 11 is the combined signal of FIGS. 7 and 8, where FIGS. 7 and 8 illustrated the real and imaginary-parts of the signal at the input of amplifier 1020. FIG. 12 is a graphical diagram illustrating the output of a chopper circuit when the input is the wave illustrated in FIG. 11. For instance, FIG. 12 is the combined signal of FIGS. 9 and 10, where FIGS. 9 and 10 illustrated the real and imaginary-parts of the signal at the output of chopper circuit 1040.

As described above, although real-part and the imaginary part of the input signal to amplifier 1020 may be as illustrated in FIGS. 7 and 8, the output of amplifier 1020 may not be an ideal rectangular wave and triangular wave due to the bandwidth of amplifier 1020. Rather, the real-part of the output signal (e.g., real-part of intermediate electrical signal) from amplifier 1020 may be trapezoidal and the imaginary-part of the output signal (e.g., imaginary-part of intermediate electrical signal) from amplifier 1020 may be triangular.

FIG. 13 is a graphical diagram illustrating the trapezoidal wave portion of the electrical signal formed at an output of an amplifier used for tissue resistance measurement. As illustrated, the real-part of the output of amplifier 1020 does not have fast rise and fall times, as compared to the rectangular wave. Rather, the signal rises slowly or falls slowly to a settling level (e.g., the same as the level of the rectangular wave). In FIG. 13, the difference between the rectangular wave and the trapezoidal wave is illustrated with the dark shading. This dark shading represents the error in the tissue resistance measurement that is caused by the bandwidth limitations of amplifier 1020 (e.g., the difference between the ideal rectangular wave and the actual trapezoidal wave that amplifier 1020 outputs). This error is a function of the frequency of the electrical signal that electrical signal source 1000 and 1010 output and chopping frequency of chopper circuit 1040.

For example, if the frequency of the electrical signal that electrical signal source 1000 and 1010 output and chopping frequency of chopper circuit 1040 is increased relative to the example illustrated in FIG. 13, then the area of the dark shaded area will increase. If the frequency of the electrical signal that electrical signal source 1000 and 1010 output and chopping frequency of chopper circuit 1040 is decreased relative to the example illustrated in FIG. 13, then the area of the dark shaded area will decrease. Also, in the illustrated example in FIG. 13, the period of the electrical signal is sufficiently large to allow the electrical signal to settle to its peak value or to its trough value. In some examples, the frequency of the electrical signal that electrical signal source 1000 and 1010 output and chopping frequency of chopper circuit 1040 should be low enough that the electrical signal that amplifier 1020 outputs settles before another rising or falling edge.

For instance, as described above, to determine the error in the tissue resistance measurement, processor 60 may determine the tissue resistance measurement at two different frequencies of the electrical signal that electrical signal source 1000 and 1010 output and of chopper circuit 1040, and perform the example computations to remove the error caused by the bandwidth limitation of amplifier 1020. The frequency of both of these tissue resistance measurements should be low enough to allow the electrical signal that amplifier 1020 outputs to settle.

FIG. 14 is a graphical diagram illustrating the triangular wave portion of the electrical signal formed at an output of an amplifier used for tissue resistance measurement. The bandwidth limitations of amplifier 1020 may also affect the imaginary-part (e.g., triangular wave portion) of the electrical signal that amplifier 1020 amplifies. For instance, in FIG. 14, the triangular wave that amplifier 1020 receives is illustrated in dashed line, and the actual triangular wave that amplifier 1020 outputs is illustrated in solid line. As can be seen, the bandwidth limitations of amplifier 1020 cause rounding on the peaks of the triangular wave.

In addition, amplifier 1020 also causes a phase delay in the output of the triangular wave as illustrated by the output of amplifier 1020 not lining up with the input of amplifier 1020. In some cases, the phase delay may be relatively small and the phase delay may not affect the tissue resistance measurement. However, in some cases, the phase delay may be relatively large, which may be another cause of error in the tissue resistance measurement.

For example, the imaginary-part output of amplifier 1020 is chopped with chopper circuit 1040 to generate the saw-tooth wave (e.g., as illustrated in FIG. 10). To generate the saw-tooth wave, chopping performed by chopper circuit 1060 should be phase aligned with the output of amplifier 1020. However, the phase delay caused by amplifier 1020 results in the chopping performed by chopper circuit 1060 to be phase misaligned with the output of amplifier 1020. This phase misalignment results in a wave that is not like a saw-tooth, but of a different shape. This different shape waveform is then integrated by averager circuit 1060.

For the saw-tooth waveform, the integration by averager circuit 1060 results in approximately zero. However, the integration by averager circuit 1060 of this non-saw-tooth shaped waveform results in a value that is not approximately zero.

In some cases, the value may be close to zero and therefore, have minimal effect, but in other cases, the value may cause additional error in the tissue resistance measurement. However, the amount of error caused by this phase delay may be determinable during manufacturing and processor 60 may then subtract this determined amount of error cause by the phase delay to more accurately determine the tissue resistance.

Also, in the example above, electrical signal sources 1000 and 1010 output an electrical signal via electrode 24A, and processor 60 determines the tissue resistance at electrode 24A. However, the output of the electrical signal via electrode 24A also causes a voltage signal to generate on other electrodes (e.g., electrodes 24B-24D). In some examples, this voltage signal generated on electrode 24B may be processed by an amplifier, a chopper circuit, and an averager circuit, like amplifier 1020, chopper circuit 1040, and averager circuit 1060 coupled to electrode 24A. Processor 60 may determine the tissue resistance at the other electrodes 24B-24D, when the current is outputted via electrode 24A, based on the output of the averager circuit for these respective electrodes 24B-24D. Processor 60 may then repeat these steps by outputting the electrical signal via electrode 24B and determining the resistance of respective electrodes 24A, 24C, and 24D, and so forth for each one of electrodes 24 to determine the tissue resistance matrix.

In the tissue resistance measurements at electrodes from which the excitation current is not being outputted, there may be no imaginary part. This is because the tissue includes no reactance components, and no current flows through the signal paths of these other electrodes, meaning there is no effect from the capacitance in the signal paths of these other electrodes. However, there may be some capacitance in the return path (e.g., capacitance between tissue and electrode on IMD 16). In some examples, the tissue resistance measurements for the other electrodes (e.g., the electrodes through which there is not an excitation current being outputted) may be more accurate than for the electrode that is outputting the excitation current because there is no imaginary part to remove. However, the error due to the limited bandwidth of their respective amplifiers would need to be removed using the example techniques described in this disclosure.

Also, in some examples, during manufacturing, a DC blocking capacitor and a capacitor to emulate the parasitic capacitance caused by tissue-electrode coupling may be connected to switch module 68 and a resistance measurement of a resistor in series to emulate the tissue resistance may be performed. The resulting error in the resistance measurement is measured, and stored into a memory (e.g., an One Time Programmable (OTP)) memory) of IMD 16. In some examples, when IMD 16 performs the resistance measurement, processor 60 corrects for the error.

For example, during manufacturing of processor 60, a resistor having a known resistance may be added to electrode 24A, and processor 60 may determine the resistance of this resistor using the techniques described in this disclosure. During manufacturing, the gain of amplifier 1020 and the amplitude of electrical signal source 1000 and 1010 can be set and the efficacy of the techniques described in this disclosure may be checked until confirmed that processor 60 determines the resistance of the resistor to equal the known resistance.

During manufacturing of processor 60, the resistor may then be replaced with a capacitor having a known capacitance (e.g., one that is approximately equal to the capacitance experienced after IMD 16 is implanted such as approximately 10 nF). In this case, processor 60 should determine the resistance to be zero. However, as described with respect to FIG. 14, the phase delay caused by amplifier 1020 may result averager circuit 1060 outputting a non-zero value. Again, under ideal case, where a 10 nF capacitor is coupled to electrode 24A, the output of chopper circuit 1040 should be a saw-tooth with average value of zero, and averager circuit 1060 would output zero. However, due to the phase delay, where a 10 nF capacitor is coupled to electrode 24A, the output of chopper circuit 1040 is not an ideal saw-tooth with average value of zero, resulting in averager circuit 1060 outputting a non-zero value.

In some examples, processor 60 may use the non-zero value to more accurately determine the tissue resistance. For example, during operation when processor 60 is determining the tissue resistance, processor 60 may account for the error in the tissue resistance cause by bandwidth limitations of amplifier 1020 by determining the tissue resistance at two different frequencies as described above. During operation when processor 60 is determining the tissue resistance, processor 60 may account for the error in the tissue resistance caused by phase delay by amplifier 1020 by subtracting this non-zero value determined during manufacturing from the tissue resistance measurement because this non-zero value was determined based on an approximation of the actual capacitance in the system.

When a few electrodes are connected in parallel, rather than in the case of a single electrode, processor 60 may not be able to compensate for this error. For example, the error will be the difference between the actual error and the amount of error correction that processor 60 applies based on stored error values. For normal resistance measurement, only a single electrode is excited at a time, and therefore, the resistance measurement may be fairly accurate by applying the compensation tested during manufacturing, as compared to attempting to compensate with many electrodes at one time. It should be understood that even in a patient-to-patient spread, the capacitance may be sufficiently close that the error is minimal.

Figure 15:
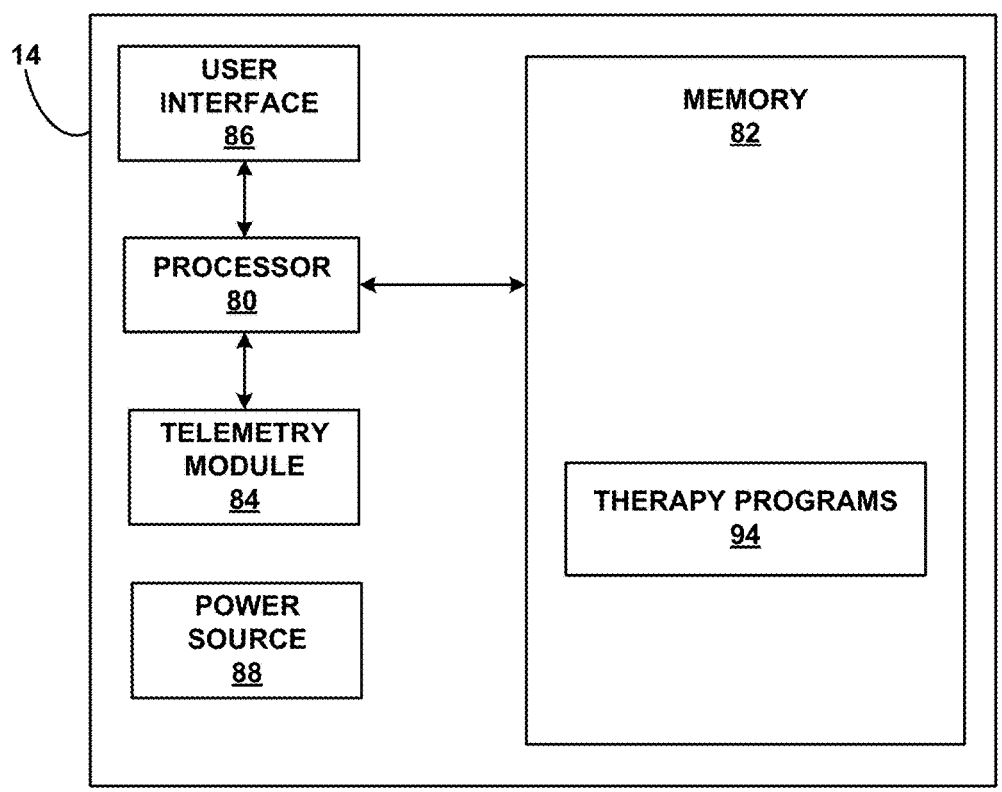
FIG. 15 is a functional block diagram illustrating components of an example medical device programmer.

FIG. 15 is a functional block diagram illustrating components of an example medical device programmer 14. Programmer 14 includes processor 80, memory 82, telemetry module 84, user interface 86, and power source 88. Processor 80 controls user interface 86 and telemetry module 84, and stores and retrieves information and instructions to and from memory 82. Programmer 14 may be configured for use as a clinician programmer or a patient programmer. Processor 80 may comprise any combination of one or more processors including one or more microprocessors, DSPs, ASICs, FPGAs, or other equivalent integrated or discrete logic circuitry. Accordingly, processor 80 may include any suitable structure, whether in hardware, software, firmware, or any combination thereof, to perform the functions ascribed herein to processor 80 and programmer 14.

A user, such as a clinician or patient 12, may interact with programmer 14 through user interface 86. User interface 86 includes a display (not shown), such as a LCD or LED display or other type of screen, with which processor 80 may present information related to the therapy (e.g., therapy programs,). In addition, user interface 86 may include an input mechanism to receive input from the user. The input mechanisms may include, for example, any one or more of buttons, a keypad (e.g., an alphanumeric keypad), a peripheral pointing device, a touch screen, or another input mechanism that allows the user to navigate though user interfaces presented by processor 80 of programmer 14 and provide input. In other examples, user interface 86 also includes audio circuitry for providing audible notifications, instructions or other sounds to patient 12, receiving voice commands from patient 12, or both.

Memory 82 may include instructions for operating user interface 86 and telemetry module 84, and for managing power source 88. Processor 80 may store the therapy programs and associated scores in memory 82 as stored therapy programs 94. A clinician may review the stored therapy programs 94 and associated scores (e.g., during programming of IMD 16) to select one or more therapy programs with which IMD 16 may deliver efficacious electrical stimulation to patient 12. For example, the clinician may interact with user interface 86 to retrieve the stored therapy programs 94 and respective scores.

In some examples, processor 80 is configured to generate and present, via a display of user interface 86, a graphical user interface (GUI) that presents a list of therapy programs and the respective scores. A user (e.g., a clinician) may interact with the GUI to manipulate the list of therapy programs. For example, in response to receiving user input requesting the list of therapy programs be ordered by score, processor 80 may reorganize the list of therapy programs based on the respective scores (e.g., from highest to lowest scores or vice versa).

In some examples, a user may also interact with the graphical user interface to select a particular therapy program, and, in response to receiving the user input, programmer 14 may provide additional details about the therapy program. For example, the additional details presented by programmer 14 may include details about the individual parameter settings of the therapy program, such as the electrical stimulation parameter values, electrode combination, or both.

In addition, in some examples, processor 80 may be configured to implement example techniques described in this disclosure. As one example, in addition to or instead of processor 60 determining a value proportional to the tissue resistance, processor 60 may output the two average values determined at the different frequencies to programmer 14. Processor 80 may determine the value proportional to the tissue resistance based on the two average values, as described above. Processor 80 may then determine the tissue resistance, and in some examples, output the tissue resistance value for user review. In some examples, processor 80 may determine therapy parameters for therapy programs 94 based on the determined tissue resistance.

In some examples, patient 12, a clinician or another user may interact with user interface 86 of programmer 14 in other ways to manually select therapy programs from the stored therapy programs 94 for programming IMD 16, generate new therapy programs, modify stored therapy programs 94, transmit the selected, modified, or new therapy programs to IMD 16, or any combination thereof.

Memory 82 may include any volatile or nonvolatile memory, such as RAM, ROM, EEPROM or flash memory. Memory 82 may also include a removable memory portion that may be used to provide memory updates or increases in memory capacities. A removable memory may also allow sensitive patient data to be removed before programmer 14 is used by a different patient.

Wireless telemetry in programmer 14 may be accomplished by RF communication or proximal inductive interaction of external programmer 14 with IMD 16. This wireless communication is possible through the use of telemetry module 84. Accordingly, telemetry module 84 may be similar to the telemetry module contained within IMD 16. In other examples, programmer 14 may be capable of infrared communication or direct communication through a wired connection. In this manner, other external devices may be capable of communicating with programmer 14 without needing to establish a secure wireless connection.

Power source 88 is configured to deliver operating power to the components of programmer 14. Power source 88 may include a battery and a power generation circuit to produce the operating power. In some examples, the battery may be rechargeable to allow extended operation. In other examples, traditional batteries (e.g., nickel cadmium or lithium ion batteries) may be used. In addition, programmer 14 may be directly coupled to an alternating current outlet to operate.

Figure 16:
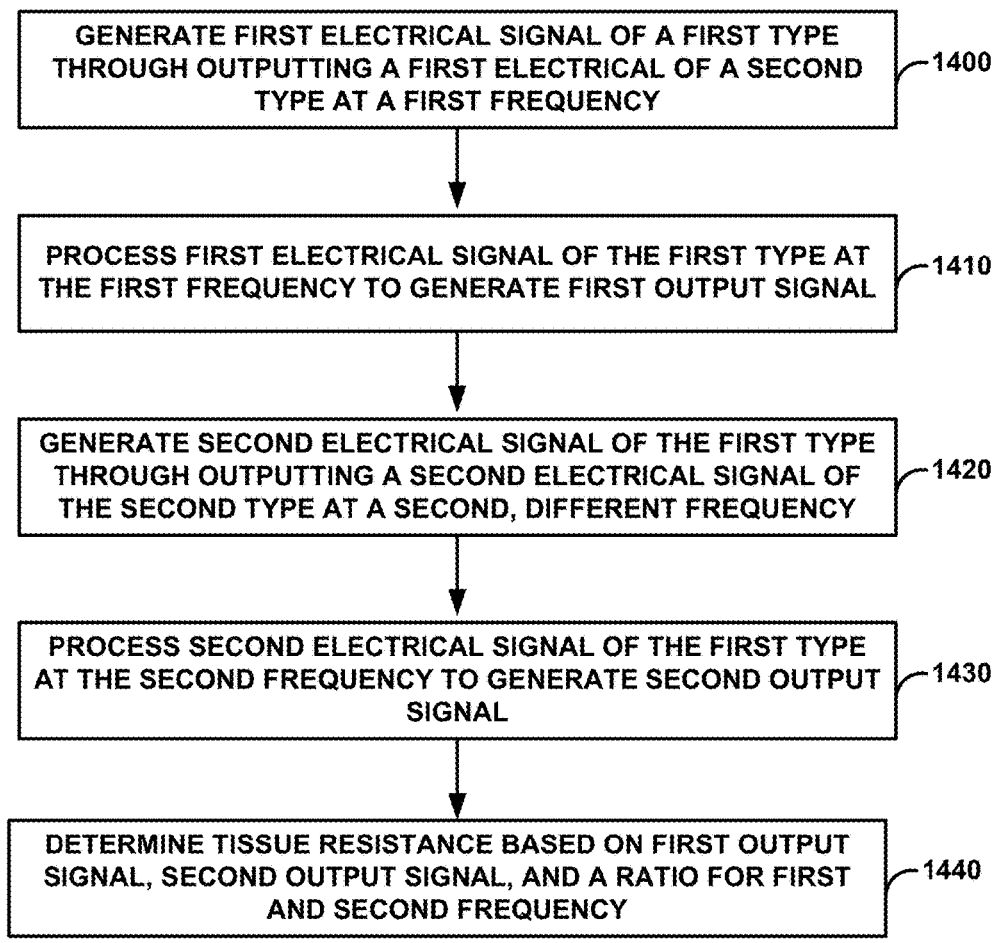
FIG. 16 is a flowchart illustrating an example technique of tissue resistance measurement.

FIG. 16 is a flowchart illustrating an example technique of tissue resistance measurement. As illustrated in FIG. 16, IMD 16 may generate, at an electrode, a first electrical signal of a first type by outputting, via the electrode, a first electrical signal of a second type at a first frequency (1400). For instance, electronic signal sources 1000 and 1010 may output, via electrode 24A, a first current signal at a first frequency to generate, at electrode 24A, a first voltage signal.

IMD 16 may process the first electrical signal of the first type at the first frequency to generate a first output signal (1410). For example, amplifier 1020, chopper circuit 1040, and averager circuit 1060 may process the first voltage signal. In this example, chopper circuit 1040 operates at the same frequency as the first frequency (e.g., 3.125 kHz). For instance, amplifier 1020 may amplify the first electrical signal of the first type to generate a first intermediate electrical signal. Chopper circuit 1040 may chop the first intermediate electrical signal at the first frequency to generate a first chopped signal. Averager circuit 1060 may average the first chopped signal to generate the first output signal, where the first output signal is a first value.

IMD 16 may generate, at the electrode, a second electrical signal of the first type by outputting, via the electrode, a second electrical signal of the second type at a second frequency (1420). For instance, electronic signal sources 1000 and 1010 may output, via electrode 24A, a second current signal at a second frequency (e.g., 6.250 kHz) to generate, at electrode 24A, a second voltage signal. IMD 16 may process the second electrical signal of the first type at the second frequency to generate a second output signal (1430). For example, amplifier 1020, chopper circuit 1040, and averager circuit 1060 may process the voltage signal. In this example, chopper circuit 1040 operates at the same frequency as the second frequency.

For instance, amplifier 1020 may amplify the second electrical signal of the first type to generate a second intermediate electrical signal. Chopper circuit 1040 may chop the second intermediate electrical signal at the second frequency to generate a second chopped signal. Averager circuit 1060 may average the second chopped signal to generate the second output signal, where the second output signal is a second value. The first value equals a value proportional to the tissue resistance plus a first error value, the second value equals the value proportional to the tissue resistance plus a second error value, and the second error value approximately equals the first error value multiplied by a ratio between the first frequency and the second frequency.

IMD 16 or programmer 14 may determine a tissue resistance at the electrode based on the first output signal, the second output signal, and a ratio between the first frequency and the second frequency (1440). For example, processor 60 or processor 80 may multiply the first output signal with the ratio between the first frequency and the second frequency, subtract the second output signal from a result of the multiplication, and determine the tissue resistance based on a result of the subtraction.

Figure 17:
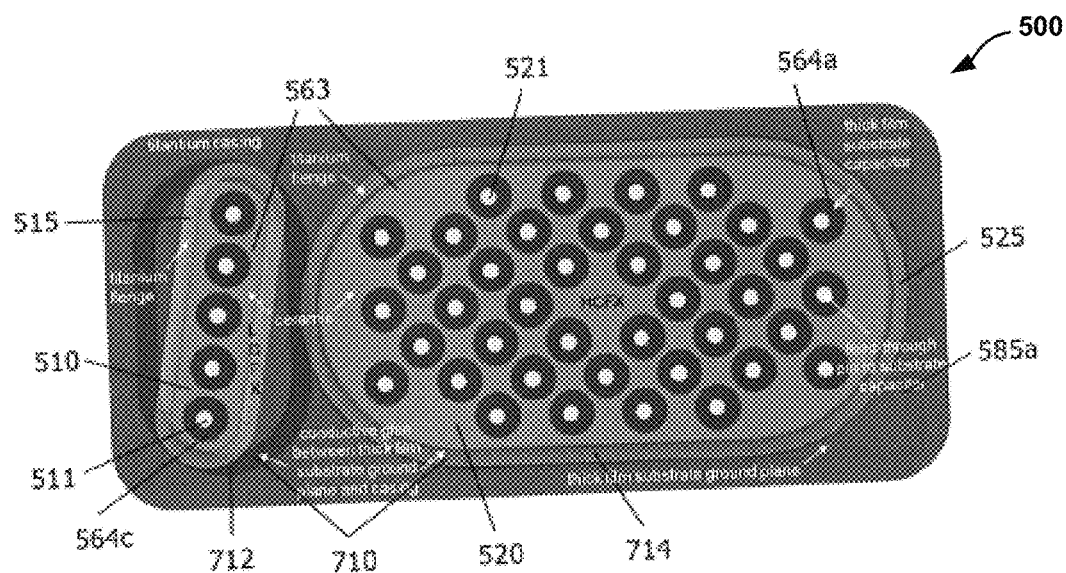
FIG. 17 is an X-ray picture of an electronic module configured to implement one or more example techniques described in this disclosure.
Figure 18:
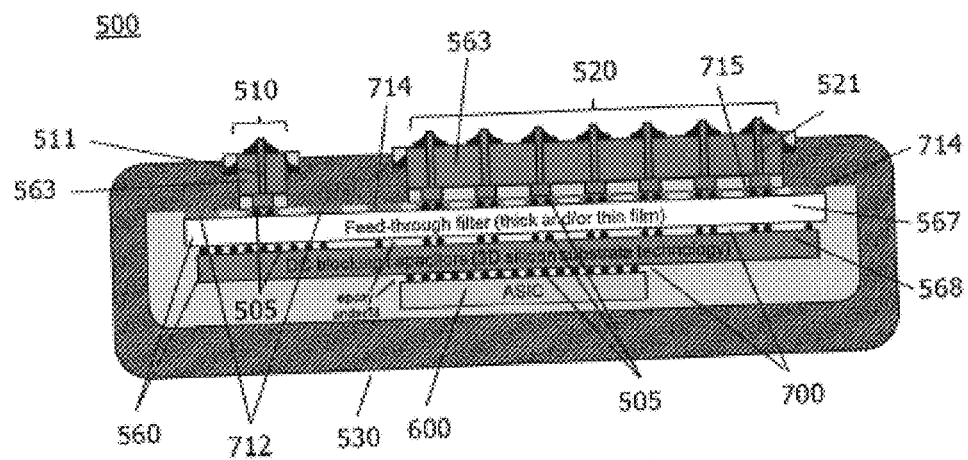
FIG. 18 is a cross-sectional view of an electronic module configured to implement one or more example techniques described in this disclosure.

FIG. 17 shows an X-ray picture of the electronic module 500. FIG. 18 shows a schematical cross-sectional view of the electronic module 500 according to one example. In the following description, FIGS. 17 and 18 are described together.

In particular, FIG. 17 shows the top feedthrough and the underlying feed through capacitor of the integrated passive device. In FIG. 17, both the connector 510 and the connector 520 on the outside as well as the top of the substrate 568 (FIG. 18) of the capacitor array on the inside, underneath the feedthrough, are shown. The ground plane of the capacitor array is electrically connected via the top part 585a of the ground plane to the housing 530 of the active lead can element 111 via a ring of conductive epoxy glue 710.

In particular, a ground ring of the connector 510 can be directly and/or indirectly electrically (galvanically, ohmically) connected to the housing 530 of the active lead can 111 via a ring of conductive epoxy glue 712 and/or a ground ring of the connector 520 can be directly and/or indirectly electrically (galvanically, ohmically) connected to the housing of the active lead can 111 via a ring of conductive epoxy glue 714. It is also possible to apply a single ring of conductive epoxy glue surrounding both connectors to electrically connect the housing 530 to the top ground plane

585*a*. If required, the feed through pins can be grouped into other combinations, in multiple sections or combined into just one single feed through.

The electronic module 500 may comprise connection pins 521 and connection pins 511. The connection pins 521 are connected to the DC blocking capacitors of integrated passive device 568 and also to the feed-through filter capacitors 564*a*. Although not explicitly shown, the connection pins 511 are also connected to integrated passive device 568 to realize the same DC blocking and EMI filtering.

Each feed-through pin 511, 521 contacts to a capacitor top contact, which can be a gold top contact, on the substrate top of thick film integrated passive device 567. The pins 521 are contacted to capacitors 564*a* and the pins 511 are contacted to capacitors 564*c*. The top contacts are simultaneously the top plates of capacitors 564*a* and capacitors 564*c*. Thus a thick film substrate with screen printed capacitors 564*a* and capacitors 564*c* forms a (single) feed-through filter substrate 567 (see e.g., FIG. 18) that is directly put on top of and connected with the feedthrough pins 511, 521.

The connector 510 has a titanium flange 515 forming a border of the connector 510 and the connector 520 has a titanium flange 525 forming a border of the connector 520. The titanium flanges are integrated in the titanium active lead can housing 530.

The electronic module 500 comprises a filtering element, wherein the filtering element is a feed-through filter 567, and a blocking element, wherein the blocking element is a DC blocking element and an ASIC 600, wherein the integrated passive device comprises the at least one filtering element, wherein the filtering element is exemplarily a feed-through filter, and/or the at least one blocking element, wherein the blocking element is exemplarily a DC blocking element. The filtering can be provided by any means which is/are capable to provide a filtering. In particular, a filtering can be provided by any passive means or passive network.

The filtering element may be configured such that interferences, in particular unwanted interferences e.g. caused by mobile phones or the like, can be removed before they may enter, e.g., a part of the housing for the electronics of the system for neural applications 100. Thereby, the advantage is achieved that a protection of the interior electronics against electromagnetic interference (EMI) is provided, for example, against mobile phone induced fields while the patient is using its mobile phone. The other way around, (high-frequency) interference generated inside the active lead can 111 is prevented from radiating outside.

The filtering element may be or may comprise e.g. an RF feed-through filter 567. The filter may comprise, e.g., a capacitor, a coil, an inductor, a resistor or any other suitable passive component. The blocking element may be configured such that in the event of a leakage current such leakage current, in particular DC leakage current flow is prevented. No DC current should flow through the patient carrying an implant such as a deep brain stimulator, even when a (single) failure occurs of, for example, the implant's electronics. This DC leakage design problem is solved by the application of DC blocking capacitors. Again, with a high number of feed-through pins 511 it may be beneficial to integrate those blocking capacitors to achieve a minimum volume and area claim as opposed to the application of discrete components.

The ASIC 600 may comprise a part or e.g. all active electronics with some external passives, for example, power supply decoupling capacitors. A substrate with integrated passives, here the integrated passive device 560, with e.g. resistors, capacitors and inductors may be used as substrate for off-chip (rerouting to) an ASIC 600. By the use of one or more application specific integrated circuits 600 the active electronic components of at least a part of the system for neural application 100 may be miniaturized.

Both for the novel feed-through filter and the DC blocking capacitor technology a substrate is used for their realization, which opens up another unique opportunity to combine all electrical and electronics components into a single stack mounted on top of the feed-through pins 511 of the connector 510 and the feed-through pins 521 of the connector 520 directly as shown in FIG. 18. This 3-layer stack with the ASIC 600 on the DC blocking element 568 achieves a very high integration density.

Electrical connections are provided via stud bumps 505, which are embedded into epoxy underfill 700. All active components of the implantable electronic device 111 (e.g., the ASIC 600) and passive (e.g. feed-through filters 567 and DC blocking capacitors) components of the active lead can 111 can be combined into a single stack and the stack can be mounted directly on top of the pins 521 of the connector 520 and the 5-pin 511 connector 510 (drawing is not true to scale).

While the techniques described above are primarily described as being performed by processor 60 of IMD 16 or processor 80 of programmer 14, in other examples, one or more other processors may perform any part of the techniques described herein alone or in addition to processor 60 or processor 80. Thus, reference to "a processor" may refer to "one or more processors." Likewise, "one or more processors" may refer to a single processor or multiple processors in different examples.

In this manner, the disclosure describes techniques related to an electronic circuit, an electronic module, an active lead can, a system and methods for determining the real part of an impedance of a first signal path for a neural application. In general, implantable neurostimulation devices have been used for the past ten years to treat acute or chronic neurological conditions. Deep brain stimulation (DBS), the mild electrical stimulation of sub-cortical structures, belongs to this category of implantable devices, and has been shown to be therapeutically effective for Parkinson's disease, Dystonia, Essential Tremor, Obsessive Compulsive Disorder, and Epilepsy. New applications of DBS in the domain of psychiatric disorders (clinical depression, anorexia nervosa, schizophrenia) are being researched. In existing systems, a lead carrying four ring electrodes at its tip is connected to an implantable pulse generator.

Currently, systems are under development with more, smaller electrodes using a technology based on thin film manufacturing. These systems include a lead made from a thin film based on thin film technology, as, e.g., described in WO 2010/055453 A1, to Koninklijke Philips Electronics, entitled "SPIRALED WIRES IN A DEEP-BRAIN STIMULATOR PROBE." The thin film carries multiple electrodes to cover the distal tip with an array of electrodes, and is assembled into a lead. Such leads will enhance the precision to address the appropriate target in the brain and relax the specification of positioning. Meanwhile, undesired side effects due to undesired stimulation of neighboring areas can be minimized. Leads that are based on thin film manufacturing are e.g. described by U.S. Pat. No. 7,941,202 by Hetke et al. and entitled "MODULAR MULTICHANNEL MICROELECTRODE ARRAY AND METHODS OF MAKING SAME" and have been used in research products in animal studies.

In existing systems, the DBS lead has e.g. four 1.5 mm-wide cylindrical electrodes at the distal end spaced by 0.5 mm or 1.5 mm. The diameter of the lead is 1.27 mm and the metal used for the electrodes and the interconnect wires is an alloy of platinum and iridium. The coiled interconnect wires are insulated individually by fluoropolymer coating and protected in a urethane tubing of a few tens of micron thick. With such electrode design, the current distribution emanates uniformly around the circumference of the electrode, which leads to stimulation of all areas surrounding the electrode.

The lack of fine spatial control over current and electric field distributions implies that stimulation easily spreads into adjacent structures inducing adverse side-effects in as much as 30% of the patients. To overcome this problem, systems with high density electrode arrays are being developed, hence providing the ability to steer the stimulation field to the appropriate target (hence the term steering brain stimulation).

The clinical benefit of DBS is largely dependent on the spatial distribution of the stimulation field in relation to brain anatomy. To maximize therapeutic benefits while avoiding unwanted side-effects, control over the stimulation field is desirable. During stimulation with existing DBS leads there is an option to use monopolar, bipolar, or even multipolar stimulation. Neurostimulator devices with steering brain stimulation capabilities can have a large number of electrode contacts (n>10) that can be connected to electrical circuits such as current sources and/or (system) ground. Stimulation may be considered monopolar when the distance between the anode and cathode is several times larger than the distance of the cathode to the stimulation target. During monopolar stimulation in homogeneous tissue the electric field is distributed roughly spherical similar to the field from a point source. When the anode is located close to the cathode the distribution of the field becomes more directed in the anode-cathode direction. As a result the field gets stronger and neurons are more likely to be activated in this area due to a higher field gradient.

Although the exact mechanisms of DBS are unknown, it is hypothesized that polarization (de- and/or hyperpolarization) of neural tissue is likely to play a prominent role both for suppression of clinical symptoms, and for induction of stimulation-induced side-effects. In order to activate a neuron it has to be depolarized. Neurons are depolarized more easily close to the cathode than by the anode (about 3-7 times more depending on type of neuron, etc.).

According to an aspect of the disclosure, electronic circuitry for determining the real part of an impedance of a first signal path of a system for neural stimulation and/or sensing applications is provided. The electronic circuit comprises a signal source. The signal source is a current source, in one example. The signal source can be configured to feed an alternating periodic stimulus signal (e.g., an alternating current) having a first frequency into the signal path. The signal can be fed into the signal path from the first end of the signal path and/or a connecting line.

The real part of the impedance of the signal path comprises all of the resistance between the signal source excitation current source (e.g. switch matrix resistance, lead track resistance and the tissue resistance itself) and a chosen return terminal (e.g. IPG and/or ALC housing), while the total capacitance comprises the total series capacitance (mainly DC blocking capacitor and electrode-tissue interface capacitance plus capacitance of the return terminal) in the loop.

The electronic circuit can further be configured to determine a magnitude of a response signal to the alternating signal (at the first end of the connecting line) and to derive the real part of the impedance from the determined magnitude. In an aspect, the electronic circuitry comprises a modulation (or de-modulation) stage, as for example a chopper stage to which the response signal is supplied. The chopper stage can then be configured to operate synchronously with the alternating signal source, i.e., at the same (first) frequency. The chopper stage can be coupled to the first end of the signal path at least somewhere between the electrode and the signal source. The chopper stage demodulates the alternating signal with the first frequency.

An instrumentation amplifier such as, for example, an operational transconductance amplifier, can be coupled between the signal path and the chopper stage. The response signal on the signal path that is an alternating voltage if the stimulus signal from the signal source is an alternating current can then be amplified and/or converted by the amplifier into a corresponding current.

The amplifier can have a settling time that is less than or equal to half the period (period relating to the first frequency) of the alternating signal. This provides that the amplifier can have reduced power consumption. These instrumentation amplifiers are often used for neural applications, in particular for neural recording. Accordingly, in an aspect of the techniques described in this disclosure, an instrumentation amplifier that is used for neural recording is used for amplifying the response of the response signal of a signal path.

In a further aspect, the amplifier may be made configurable to have a first bandwidth for a neural application, as for example neural recording and a second bandwidth if it is used for amplifying the response signal on the signal path. This allows reusing most of the components, if not all, of the amplifier and avoids implementation of several amplifiers for the measurement of the real part of the impedance of the signal paths.

The output signal of the chopper stage can be fed to an analog-to-digital converter. This way the output signal can be converted into a digital signal. The output signal is a representation of the real part of the impedance within certain limits of accuracy. Accordingly, an analog-to-digital converter (ADC) can be provided and be coupled to the output of the chopper stage. The ADC may be an averaging ADC. This means that the signal undergoes an integration/low pass function, thereby suppressing noise and/or eliminating artifacts, errors and/or other deficiencies of the electronic stages preceding the ADC.

In an example, the electronic circuit can further be configured to consecutively feed the alternating signal to the first signal path and to a second signal path comprising a second connecting line, a second electrode and human tissue to which the second electrode is coupled for individually determining the real part of the impedance of the first signal path and the real part of the impedance of the second signal path, respectively. In general, the electronic circuit can be figured to supply the alternating signal into any number of signal paths, each signal path having an electrode being in contact with human tissue. The electronic circuit is then configured to consecutively supply at least one signal path with the alternating (current) signal and to measure the response for each signal path (i.e. each channel) thereby determining the respect real parts of each signal path. Each real part substantially represents the resistance of the human tissue to which the electrode is coupled.

If a plurality of signal paths is measured in accordance with the aspects and techniques described in this disclosure, the electronic circuitry may comprise a matrix of switches for feeding the alternating signal to the different signal paths. This switch matrix may, for example be a switch matrix that is already provided for coupling different signal paths to the same pulse generating source.

The alternating signal can be configured to symmetrically alternate around a ground level with the first frequency, such that the a full period of the alternating signal substantially has no DC content with respect to the ground level. The alternating signal can be a square wave signal that is symmetric around ground. If this kind of signal is processed by the chopper stage, the signal components relating to capacitances in the signal path can be eliminated.

The signal source can be a push-pull current source alternately supplying a first current having a first magnitude and a second current having the same (first) magnitude but flowing in opposite direction than the first current. The push-pull current source can comprise two complementary current sources being alternately switched to supply the first and second current to the signal path. Such a push-pull current source is suitable to be integrated in an integrated circuit and generally constitutes a robust and simple implementation of the signal source.

In an aspect, the signal source can be configured to alternate the alternating signal at the first frequency and at a second frequency that is different from the first frequency. The frequency of the alternating may repeatedly and/or periodically be changed. This aspect provides that errors due to limited settling behavior and bandwidth of the components can be reduced.

The first frequency can be between 1 kHz and 100 kHz; however, other ranges are possible, and the techniques described in this disclosure should not be considered limited to the example frequency range. The second frequency can be different from the first frequency by 1 kHz to 10 kHz; however, other ranges are possible, and the techniques described in this disclosure should not be considered limited to the example frequency range.

The magnitude of the currents supplied by the signal source can be substantially smaller than any stimulation signals for the neural applications. The amplitude of the alternating signal can be approximately 8 micro-amps, but other current amplitudes are possible. Any signal path can comprise the at least one connecting line coupled to the signal source at a first end, and an electrode coupled to a second end of the connecting line opposite to the first end and human tissue to which the electrode is coupled. The connecting line and/or the signal path can comprise cables, wires, interconnects, switches, resistors, integrated components and wires as well as bond pads, bonding wires etc.

Any connecting line of a signal path can comprise at least one or more of a blocking capacitor, a switch, a connector, a bond pad, etc. This provides a comparably small size and still sufficient DC decoupling.

The present technique may also provide an electronic module comprising the electronic circuitry according to the aspects and examples described in this disclosure. The present techniques may also provide an active lead can that comprises the electronic circuitry and/or the electronic module according to the aspects and/or examples described in this disclosure. The present techniques may also provide a system for neural applications comprising an electronic circuit and/or an electronic module and/or an active lead can and/or a pulse generating device according to the aspects and examples described in this disclosure. The system also includes the signal path at least up to the electrode.

The present techniques may further provide methods of operating an electronic circuitry, an electronic module, an ALC and/or a system in accordance with the aspects and/or examples described in this disclosure. The techniques may also provide a method of determining a real part of an impedance of a signal path for a neural application. Accordingly, an alternating signal can be injected into a first signal path comprising a first electrode coupled to human tissue. The response signal (of the signal path) to the alternating signal can then be chopped synchronously to the alternating signal and the real part of the impedance of the first signal path can be determined based on the chopped response signal. Other aspects of this method can be derived from the aspects and examples of the electronic circuit, system etc. as described herein.

The techniques described in this disclosure, including those attributed to IMD 16, programmer 14, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as clinician or patient programmers, medical devices, or other devices.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various examples have been described. These and other examples are within the scope of the following claims.

What is claimed is:

1. A method for tissue resistance measurement, the method comprising:

generating, at an electrode, a first electrical signal of a first type through outputting, via the electrode, a first electrical signal of a second type at a first frequency;

processing, at least in part with a bandwidth-limited amplifier, the first electrical signal of the first type at the first frequency to generate a first output signal, wherein processing the first electrical signal comprises amplifying, with the amplifier, the first electrical signal of the first type to generate a first intermediate electrical signal, and wherein a slew rate of the first intermediate electrical signal generated by the amplifier is less than a slew rate of a rectangular wave;

generating, at the electrode, a second electrical signal of the first type through outputting, via the electrode, a second electrical signal of the second type at a second, different frequency;

processing, at least in part with the bandwidth-limited amplifier, the second electrical signal of the first type at the second frequency to generate a second output signal, wherein processing the second electrical signal comprises amplifying, with the amplifier, the second electrical signal of the first type to generate a second intermediate electrical signal, and wherein a slew rate of the second intermediate electrical signal generated by the amplifier is less than the slew rate of the rectangular wave; and determining a tissue resistance at the electrode based on the first output signal, the second output signal, and a ratio between the first frequency and the second frequency, wherein the ratio includes a value based on a division of a value based on the first frequency and a value based on the second frequency.

2. The method of claim 1, wherein the first electrical signal of the first type comprises a first voltage signal, wherein the first electrical signal of the second type comprises a first current signal, wherein the second electrical signal of the first type comprises a second voltage signal, and wherein the second electrical signal of the second type comprises a second current signal.

3. The method of claim 1,
wherein processing the first electrical signal of the first type comprises:
chopping the first intermediate electrical signal at the first frequency to generate a first chopped signal; and
averaging the first chopped signal to generate the first output signal, wherein the first output signal is a first value, and
wherein processing the second electrical signal of the first type comprises:
chopping the second intermediate electrical signal at the second frequency to generate a second chopped signal; and
averaging the second chopped signal to generate the second output signal, wherein the second output signal is a second value.

4. The method of claim 3, wherein the amplifier comprises a transconductance amplifier, wherein amplifying the first electrical signal of the first type comprises amplifying the first electrical signal with the transconductance amplifier, and wherein amplifying the second electrical signal of the first type comprises amplifying the second electrical signal with the transconductance amplifier.

5. The method of claim 3, wherein the first value equals a value proportional to the tissue resistance plus a first error value, wherein the second value equals the value proportional to the tissue resistance plus a second error value, and wherein the second error value approximately equals the first error value multiplied by a ratio between the first frequency and the second frequency.

6. The method of claim 1, wherein determining the tissue resistance comprises:
multiplying the first output signal with the ratio between the first frequency and the second frequency;
subtracting the second output signal from a result of the multiplication; and
determining the tissue resistance based on a result of the subtraction.

7. The method of claim 1, wherein the first electrical signal of the first type comprises a first rectangular-wave electrical signal and a first triangular-wave electrical signal having a frequency equal to the first frequency, wherein the second electrical signal of the first type comprises a second rectangular-wave electrical signal and a second triangular-wave electrical signal having a frequency equal to the second frequency, wherein the first rectangular-wave electrical signal and the second rectangular-wave electrical signal are generated from resistance in a signal path of the first electrical signal of the second type and the second electrical signal of the second type, respectively, and wherein the first triangular-wave electrical signal and the second triangular-wave electrical signal are generated from reactance in the signal path of the first electrical signal of the second type and the second electrical signal of the second type, respectively.

8. A system for tissue resistance measurement, the system comprising:
at least one electrical signal source configured to:
generate, at an electrode, a first electrical signal of a first type through outputting, via the electrode, a first electrical signal of a second type at a first frequency; and
generate, at the electrode, a second electrical signal of the first type through outputting, via the electrode, a second electrical signal of the second type at a second, different frequency;
resistance measurement circuitry configured to:
process, at least in part with a bandwidth-limited amplifier, the first electrical signal of the first type at the first frequency to generate a first output signal, wherein, to process the first electrical signal, the amplifier is configured to amplify the first electrical signal of the first type to generate a first intermediate electrical signal, and wherein a slew rate of the first intermediate electrical signal generated by the amplifier is less than a slew rate of a rectangular wave; and
process, at least in part with the bandwidth-limited amplifier, the second electrical signal of the first type at the second frequency to generate a second output signal wherein, to process the second electrical signal, the amplifier is configured to amplify the second electrical signal of the first type to generate a second intermediate electrical signal, and wherein a slew rate of the second intermediate electrical signal generated by the amplifier is less than the slew rate of the rectangular wave; and
a processor configured to determine a tissue resistance at the electrode based on the first output signal, the second output signal, and a ratio between the first frequency and the second frequency, wherein the ratio includes a value based on a division of a value based on the first frequency and a value based on the second frequency.

9. The system of claim 8, further comprising an implantable medical device (IMD), the IMD comprising the at least one electrical signal source, the resistance measurement circuitry, and the processor.

10. The system of claim 8, further comprising an implantable medical device (IMD) and a programmer, the IMD comprising the at least one electrical signal source and the resistance measurement circuitry, and wherein the programmer comprises the processor.

11. The system of claim 8, wherein the first electrical signal of the first type comprises a first voltage signal, wherein the first electrical signal of the second type comprises a first current signal, wherein the second electrical signal of the first type comprises a second voltage signal, and wherein the second electrical signal of the second type comprises a second current signal.

12. The system of claim 8, wherein resistance measurement circuitry comprises:
a chopper circuit configured to chop the first intermediate electrical signal at the first frequency to generate a first chopped signal, and chop the second intermediate electrical signal at the second frequency to generate a second chopped signal; and
an averager circuit configured to average the first chopped signal to generate the first output signal, wherein the first output signal is a first value, and average the second chopped signal to generate the second output signal, wherein the second output signal is a second value.

13. The system of claim 12, wherein the amplifier is configured to amplify neural recoding signals.

14. The system of claim 12, wherein the first value equals a value proportional to the tissue resistance plus a first error value, wherein the second value equals the value proportional to the tissue resistance plus a second error value, and wherein the second error value approximately equals the first error value multiplied by a ratio between the first frequency and the second frequency.

15. The system of claim 12, wherein to determine the tissue resistance, the processor is configured to:
multiply the first output signal with the ratio between the first frequency and the second frequency;
subtract the second output signal from a result of the multiplication; and
determine the tissue resistance based on a result of the subtraction.

16. The system of claim 8, wherein the first electrical signal of the first type comprises a first rectangular-wave electrical signal and a first triangular-wave electrical signal having a frequency equal to the first frequency, wherein the second electrical signal of the first type comprises a second rectangular-wave electrical signal and a second triangular-wave electrical signal having a frequency equal to the second frequency, wherein the first rectangular-wave electrical signal and the second rectangular-wave electrical signal are generated from resistance in a signal path of the first electrical signal of the second type and the second electrical signal of the second type, respectively, and wherein the first triangular-wave electrical signal and the second triangular-wave electrical signal are generated from reactance in the signal path of the first electrical signal of the second type and the second electrical signal of the second type, respectively.

17. A system for tissue resistance measurement, the system comprising:
means for generating, at an electrode, a first electrical signal of a first type through outputting, via the electrode, a first electrical signal of a second type at a first frequency;
means for processing the first electrical signal of the first type at the first frequency to generate a first output signal, wherein the means for processing the first electrical signal of the first type comprises means for amplifying the first electrical signal of the first type to generate a first intermediate electrical signal, and wherein a slew rate of the first intermediate electrical signal is less than a slew rate of a rectangular wave;
means for generating, at the electrode, a second electrical signal of the first type through outputting, via the electrode, a second electrical signal of the second type at a second, different frequency;
means for processing the second electrical signal of the first type at the second frequency to generate a second output signal, wherein the means for processing the second electrical signal of the first type comprises means for amplifying the second electrical signal of the first type to generate a second intermediate electrical signal, and wherein a slew rate of the second intermediate electrical signal is less than the slew rate of the rectangular wave; and
means for determining a tissue resistance at the electrode based on the first output signal, the second output signal, and a ratio between the first frequency and the second frequency wherein the ratio includes a value based on a division of a value based on the first frequency and a value based on the second frequency.

18. The system of claim 17,
wherein the means for processing the first electrical signal of the first type comprises:
means for chopping the first intermediate electrical signal at the first frequency to generate a first chopped signal; and
means for averaging the first chopped signal to generate the first output signal, wherein the first output signal is a first value, and
wherein the means for processing the second electrical signal of the first type comprises:
means for chopping the second intermediate electrical signal at the second frequency to generate a second chopped signal; and
means for averaging the second chopped signal to generate the second output signal, wherein the second output signal is a second value.

19. The system of claim 17, wherein the means for determining the tissue resistance comprises:
means for multiplying the first output signal with the ratio between the first frequency and the second frequency;
means for subtracting the second output signal from a result of the multiplication; and
means for determining the tissue resistance based on a result of the subtraction.

20. The system of claim 17, wherein the first electrical signal of the first type comprises a first rectangular-wave electrical signal and a first triangular-wave electrical signal having a frequency equal to the first frequency, wherein the second electrical signal of the first type comprises a second rectangular-wave electrical signal and a second triangular-wave electrical signal having a frequency equal to the second frequency, wherein the first rectangular-wave electrical signal and the second rectangular-wave electrical signal are generated from the tissue resistance, and wherein the first triangular-wave electrical signal and the second triangular-wave electrical signal are generated from reactance in a signal path of the first electrical signal of the second type and the second electrical signal of the second type, respectively.

* * * * *